United States Patent
Foley et al.

(10) Patent No.: US 12,391,688 B2
(45) Date of Patent: Aug. 19, 2025

(54) IMIDAZOPYRIDINE DERIVATIVES AS IL-17 MODULATORS

(71) Applicant: UCB Biopharma SRL, Brussels (BE)

(72) Inventors: Anne Marie Foley, Slough (GB); Fabien Claude Lecomte, Slough (GB); James Thomas Reuberson, Slough (GB); Matthew Duncan Selby, Slough (GB); Richard David Taylor, Slough (GB); Paul Jonathan Hickford, Abingdon (GB); Gareth Neil Brace, Abingdon (GB)

(73) Assignee: UCB Biopharma SRL, Brussels (BE)

( * ) Notice: Subject to any disclaimer, the term of this patent is extended or adjusted under 35 U.S.C. 154(b) by 783 days.

(21) Appl. No.: 17/614,067

(22) PCT Filed: Jun. 24, 2020

(86) PCT No.: PCT/IB2020/055970
§ 371 (c)(1),
(2) Date: Nov. 24, 2021

(87) PCT Pub. No.: WO2020/261141
PCT Pub. Date: Dec. 30, 2020

(65) Prior Publication Data
US 2022/0227764 A1    Jul. 21, 2022

(30) Foreign Application Priority Data

Jun. 26, 2019 (GB) ...................................... 1909190

(51) Int. Cl.
*C07D 471/04* (2006.01)
(52) U.S. Cl.
CPC ................................. *C07D 471/04* (2013.01)
(58) Field of Classification Search
CPC .................................................. C07D 471/04
See application file for complete search history.

(56) References Cited

U.S. PATENT DOCUMENTS

| | | | | |
|---|---|---|---|---|
| 8,436,043 B2 * | 5/2013 | Banno | ................ | C07D 491/048 549/467 |
| 8,629,147 B2 * | 1/2014 | Anikin | ................ | C07D 401/04 514/253.09 |
| 2005/0203078 A1 † | 9/2005 | Priepke | | |
| 2011/0245257 A1 | 10/2011 | Cushing et al. | | |
| 2012/0053173 A1 | 3/2012 | Banno et al. | | |
| 2022/0073526 A1 † | 3/2022 | Coates | | |
| 2024/0140951 A1 * | 5/2024 | Brace | ................ | C07D 519/00 |
| 2024/0294534 A1 * | 9/2024 | Brace | ................ | A61P 37/00 |

FOREIGN PATENT DOCUMENTS

| | | |
|---|---|---|
| CN | 101103022 A | 1/2008 |
| WO | 2005/082895 | 9/2005 |
| WO | 2007/002701 | 1/2007 |
| WO | 2009110520 | 9/2009 |
| WO | 2010/129500 | 11/2010 |
| WO | 2013/116682 | 8/2013 |
| WO | 2014/066726 | 5/2014 |
| WO | 2014210159 | 12/2014 |
| WO | 2018/229079 | 12/2018 |
| WO | 2019/138017 | 7/2019 |
| WO | 2020146194 | 7/2020 |
| WO | 2021220183 | 11/2021 |
| WO | 2021222404 | 11/2021 |

OTHER PUBLICATIONS

PubChem CID 33845133, National Center for Biotechnology Information. PubChem Compound Summary for CID 33845133, 2-Benzylimidazo[1,2-a]pyridine. https://pubchem.ncbi.nlm.nih.gov/compound/2-Benzylimidazo_1_2-a_pyridine. Accessed Aug. 23, 2024, create date May 29, 2009. (Year: 2009).*
Chemical Abstracts Registry No. 2320819-04-1, indexed in the Registry file on STN CAS Online May 30, 2019. (Year: 2019).*
PubChem CID 7150712, National Center for Biotechnology Information. PubChem Compound Summary for CID 7150712, N-((7-methylimidazo[1,2-a]pyridin-2-yl)methyl)thiophene-2-carboxamide. https://pubchem.ncbi.nlm.nih.gov/compound/7150712. Accessed Oct. 16, 2024, create date Jul. 29, 2006. (Year: 2006).*
PubChem CID 50973771, National Center for Biotechnology Information. PubChem Compound Summary for CID 50973771, 5-isopropyl-N-[(7-methylimidazo[1,2-a]pyridin-2-yl)methyl]isoxazole-3-carboxamide. https://pubchem.ncbi.nlm.nih.gov/compound/50973771. Accessed Oct. 16, 2024, create date Mar. 29, 2011. (Year: 2011).*
English Translation of Notification of Reasons for Rejection for Japanese Patent Application No. 2021-571604 dated Mar. 28, 2024, pp. 1-6.
Gaffen, Sarah L., An overview of IL-17 function and signaling, Cytokine, 2008, 402-407, 43.

(Continued)

*Primary Examiner* — Laura L Stockton
(74) *Attorney, Agent, or Firm* — McDonnell Boehnen Hulbert & Berghoff LLP

(57) ABSTRACT

A series of substituted fused bicyclic imidazole derivatives, including imidazo[1,2-a]pyridine derivatives and analogues thereof, being potent modulators of human IL-17 activity, are accordingly of benefit in the treatment and/or prevention of various human ailments, including inflammatory and autoimmune disorders.

10 Claims, No Drawings

(56) References Cited

OTHER PUBLICATIONS

Korn et al, IL-17 and Th17 Cells, Annu. Rev. Immunol., 2009, 485-517, 27.

Koster H et al, A small nonrule of three compatable fragment library provides high hit rate of Endothiapepsin crystal structures with various fragment chemotypes, Journal of Medicinal Chemistry, Nov. 24, 2011, 7784-7796, vol. 54 No. 22.

Moseley et al, Interleukin-17 family and IL-17 receptors, Cytokine Growth Factor Rev, 2003, 155-174, 14.

P.H. Stahl & C.G. Wermuth, Handbook of Pharmaceutical Salts: Properties, Selection and Use, 2002.

Rouvier et al, CTLA-8, cloned from an activated T cell, bearing AU-rich messenger RNA instability sequences, and homologous to a herpesvirus saimiri gene, J. Immunol, 1993, 5445-5456, 150.

Sandeep Yadav, The influence of charge distribution on self-association and viscosity behavior of monoclonal antibody solutions, Molecar Pharmaceutics, 2012, 791-802, 9.

Shin Y et al, Discovery, Optimisation, and in Vivo evaluation of Benzimidazole derivatives AM-8505 and AM-9635 as potent and selective PI3K[delta] inhibitors, Journal of Medicinal Chemistry, Dec. 21, 2015, 431-447, vol. 59 No. 1.

Wright et al, The human IL17/IL-17A Heterodimeric Cytokine Signals through the IL-17RA/IL-17RC Receptor Complex, J. Immunol, 2008, 2799-2805, 181.

Yadav, J. S. et al. "Cu(OTf)2-catalyzed synthesis of imidazol [1.2-a]pyridines from alpha-diazoketones and 2-aminopyridines" Tetrahedron Letters (2007) vol. 48, pp. 7717-7720.

A Small Nonrule of 3 Compatible Fragment Library Provides High Hit Rate of Endothiapepsin Crystal Structures with Various Fragment Chemotypes Helene Koster, Tobias Craan, Sascha Brass, Christian Herhaus, Matthias Zentgraf, Lars Neumann, Andreas Heine, and Gerhard Klebe J. Med. Chem. 2011, 54, 77847796.†

\* cited by examiner

† cited by third party

IMIDAZOPYRIDINE DERIVATIVES AS IL-17 MODULATORS

CROSS-REFERENCE TO RELATED APPLICATIONS

This application is a U.S. national phase of International Application No. PCT/IB2020/055970, filed Jun. 24, 2020, which claims priority from Great Britain application no. GB 1909190.9, filed June 26.

The present invention relates to heterocyclic compounds, and to their use in therapy. More particularly, this invention is concerned with pharmacologically active substituted fused bicyclic imidazole derivatives, including imidazo[1,2-a]pyridine derivatives and analogues thereof. These compounds act as modulators of IL-17 activity, and are accordingly of benefit as pharmaceutical agents for the treatment and/or prevention of pathological conditions, including adverse inflammatory and autoimmune disorders.

IL-17A (originally named CTLA-8 and also known as IL-17) is a pro-inflammatory cytokine and the founder member of the IL-17 family (Rouvier et al., *J. Immunol.*, 1993, 150, 5445-5456). Subsequently, five additional members of the family (IL-17B to IL-17F) have been identified, including the most closely related, IL-17F (ML-1), which shares approximately 55% amino acid sequence homology with IL-17A (Moseley et al., *Cytokine Growth Factor Rev.*, 2003, 14, 155-174). IL-17A and IL-17F are expressed by the recently defined autoimmune related subset of T helper cells, Th17, that also express IL-21 and IL-22 signature cytokines (Korn et al., *Ann. Rev. Immunol.*, 2009, 27, 485-517). IL-17A and IL-17F are expressed as homodimers, but may also be expressed as the IL-17A/F heterodimer (Wright et al., *J. Immunol.*, 2008, 181, 2799-2805). IL-17A and F signal through the receptors IL-17R, IL-17RC or an IL-17RA/RC receptor complex (Gaffen, *Cytokine*, 2008, 43, 402-407). Both IL-17A and IL-17F have been associated with a number of autoimmune diseases.

The compounds in accordance with the present invention, being potent modulators of human IL-17 activity, are therefore beneficial in the treatment and/or prevention of various human ailments, including inflammatory and autoimmune disorders.

Furthermore, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/116682 and WO 2014/066726 relate to separate classes of chemical compounds that are stated to modulate the activity of IL-17 and to be useful in the treatment of medical conditions, including inflammatory diseases.

WO 2018/229079 describes a class of spirocyclic oxindoline derivatives, and analogues thereof, that are stated to act as modulators of IL-17 activity, and thus to be of benefit in the treatment of pathological conditions including adverse inflammatory and autoimmune disorders.

Co-pending international patent application PCT/EP2019/050594 (published on 18 Jul. 2019 as WO 2019/138017) describes a class of fused bicyclic imidazole derivatives, including benzimidazole derivatives and analogues thereof, that are stated to act as modulators of IL-17 activity, and thus to be of benefit in the treatment of pathological conditions including adverse inflammatory and autoimmune disorders.

None of the prior art available to date, however, discloses or suggests the precise structural class of substituted imidazo[1,2-a]pyridine derivatives, and analogues thereof, as provided by the present invention.

The present invention provides a compound of formula (I) or an N-oxide thereof, or a pharmaceutically acceptable salt thereof:

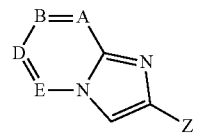

(I)

wherein
A represents C—$R^1$ or N;
B represents C—$R^2$ or N;
D represents C—$R^3$ or N;
E represents C—$R^4$ or N;
Z represents —CH($R^5$)N(H)C(O)$R^6$, —CH($R^5$)N(H)S(O)$_2R^6$, —C(=C$R^{5a}R^{5b}$)N(H)C(O)$R^6$, —CH($R^5$)$R^7$, —CH($R^5$)N(H)$R^7$ or —CH($R^5$)C(O)N(H)$R^7$;
$R^1$, $R^2$, $R^3$ and $R^4$ independently represent hydrogen, halogen, cyano, nitro, hydroxy, trifluoromethyl, trifluoromethoxy, —O$R^a$, —S$R^a$, —SO$R^a$, —SO$_2R^a$, —N$R^bR^c$, —N$R^cCOR^d$, —N$R^cCO_2R^d$, —NHCON$R^bR^c$, —N$R^cSO_2R^e$, —NHSO$_2$N$R^bR^c$, —N=S(O)$R^bR^c$, —CO$R^d$, —CO$_2R^d$, —CON$R^bR^c$, —CON(O$R^a$)$R^b$, —SO$_2$N$R^bR^c$ or —S(O)(N$R^c$)$R^a$; or $C_{1-6}$ alkyl, $C_{2-6}$ alkenyl, $C_{2-6}$ alkynyl, $C_{3-9}$ cycloalkyl, $C_{3-9}$ cycloalkyl($C_{1-6}$)alkyl, $C_{4-9}$ cycloalkenyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl or heteroaryl($C_{1-6}$)alkyl, any of which groups may be optionally substituted by one or more substituents;

$R^5$ represents hydrogen; or $R^5$ represents $C_{1-6}$ alkyl, $C_{3-9}$ cycloalkyl, $C_{3-9}$ cycloalkyl($C_{1-6}$)alkyl, $C_{4-9}$ cycloalkenyl, $C_{4-12}$ bicycloalkyl, $C_{5-9}$ spirocycloalkyl, $C_{5-9}$ spirocycloalkyl($C_{1-6}$)alkyl, $C_{8-11}$ tricycloalkyl, $C_{8-11}$ tricycloalkyl($C_{1-6}$)alkyl, $C_{7-13}$ dispirocycloalkyl, $C_{7-13}$ dispirocycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^{5a}$ represents $C_{3-7}$ cycloalkyl, $C_{4-9}$ bicycloalkyl, aryl, $C_{3-7}$ heterocycloalkyl or heteroaryl, any of which groups may be optionally substituted by one or more substituents; and $R^{5b}$ represents hydrogen or $C_{1-6}$ alkyl; or
$R^{5a}$ and $R^{5b}$, when taken together with the carbon atom to which they are both attached, represent $C_{3-7}$ cycloalkyl, $C_{4-9}$ bicycloalkyl or $C_{3-7}$ heterocycloalkyl, any of which groups may be optionally substituted by one or more substituents;

$R^6$ represents —O$R^{6a}$ or —N$R^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents;

$R^{6a}$ represents $C_{1-6}$ alkyl; or $R^{6a}$ represents $C_{3-9}$ cycloalkyl, which group may be optionally substituted by one or more substituents;

$R^{6b}$ represents hydrogen or $C_{1-6}$ alkyl;
$R^{6c}$ represents hydrogen or $C_{1-6}$ alkyl;

R[7] represents aryl, heteroaryl or spiro[($C_{3-7}$)heterocycloalkyl][heteroaryl], any of which groups may be optionally substituted by one or more substituents;

R[a] represents trifluoromethyl; or R[a] represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents;

R[b] and R[c] independently represent hydrogen or trifluoromethyl; or $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or R[b] and R[c], when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R[d] represents hydrogen; or R[d] represents $C_{1-6}$ alkyl, $C_{3-9}$ cycloalkyl, aryl, $C_{3-7}$ heterocycloalkyl or heteroaryl, any of which groups may be optionally substituted by one or more substituents; and R[e] represents $C_{1-6}$ alkyl, aryl or heteroaryl, any of which groups may be optionally substituted by one or more substituents.

The present invention also provides a compound of formula (I) as defined above, or a pharmaceutically acceptable salt thereof.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of IL-17 function is indicated.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of IL-17 function is indicated.

The present invention also provides a method for the treatment and/or prevention of disorders for which the administration of a modulator of IL-17 function is indicated which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of formula (I) include acid addition salts which may, for example, be formed by mixing a solution of a compound of formula (I) with a solution of a pharmaceutically acceptable acid.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl and allyl.

Suitable $C_{2-6}$ alkynyl groups include ethynyl and propargyl.

The term "$C_{3-9}$ cycloalkyl" as used herein refers to monovalent groups of 3 to 9 carbon atoms derived from a saturated monocyclic hydrocarbon, and may comprise benzo-fused analogues thereof. Suitable $C_{3-9}$ cycloalkyl groups include cyclopropyl, cyclobutyl, benzocyclobutenyl, cyclopentyl, indanyl, cyclohexyl, cycloheptyl, cyclooctyl and cyclononanyl.

The term "$C_{4-9}$ cycloalkenyl" as used herein refers to monovalent groups of 4 to 9 carbon atoms derived from an unsaturated monocyclic hydrocarbon, and may comprise benzo-fused analogues thereof. Suitable $C_{4-9}$ cycloalkenyl groups include cyclobutenyl, cyclopentenyl, cyclohexenyl, cycloheptenyl and cyclooctenyl.

The term "$C_{4-12}$ bicycloalkyl" as used herein refers to monovalent groups of 4 to 12 carbon atoms derived from a saturated bicyclic hydrocarbon. Typical bicycloalkyl groups include bicyclo[1.1.1]pentanyl, bicyclo[3.1.0]hexanyl, bicyclo[4.1.0]heptanyl and bicyclo[2.2.2]octanyl.

The term "$C_{5-9}$ spirocycloalkyl" as used herein refers to saturated bicyclic ring systems containing 5 to 9 carbon atoms, in which the two rings are linked by a common atom. Suitable spirocycloalkyl groups include spiro[2.3]hexanyl, spiro[2.4]heptanyl, spiro[3.3]heptanyl, spiro[3.4]octanyl, spiro[3.5]nonanyl and spiro[4.4]nonanyl.

The term "$C_{8-11}$ tricycloalkyl" as used herein refers to monovalent groups of 8 to 11 carbon atoms derived from a saturated tricyclic hydrocarbon. Typical tricycloalkyl groups include adamantanyl.

The term "$C_7$-13 dispirocycloalkyl" as used herein refers to saturated tricyclic ring systems containing 7 to 13 carbon atoms, in which the three rings incorporate two spiro linkages. Suitable dispirocycloalkyl groups include dispiro[2.0.24.13]heptanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzofuranyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]-pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include 2,5-dihydropyrrolyl, thiazolinyl, imidazolinyl, dihydropyranyl, dihydrothiopyranyl, 1,2-dihydropyridinyl, 1,2,3,4-tetrahydropyridinyl, 1,2,3,6-tetrahydropyridinyl, 2,3-dihydro-1,4-oxazinyl and 6,7-dihydro-5H-1,4-oxazepinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 6-oxabicyclo[3.1.0]hexanyl, 3-azabicyclo[3.1.0]hexanyl, 2-oxa-5-azabicyclo[2.2.1]-heptanyl, 6-azabicyclo[3.2.0]heptanyl, 6-oxabicyclo[3.1.1] heptanyl, 3-azabicyclo[3.1.1]-heptanyl, 3-azabicyclo[4.1.0] heptanyl, 2-oxabicyclo[2.2.2]octanyl, quinuclidinyl, 2-oxa-5-azabicyclo[2.2.2]octanyl, 8-oxabicyclo[3.2.1]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]-octanyl, 3,6-diazabicyclo[3.2.2]nonanyl, 3-oxa-7-azabicyclo[3.3.1]nonanyl, 3,7-dioxa-9-azabicyclo[3.3.1]nonanyl and 3,9-diazabicyclo[4.2.1]nonanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b]-[1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]-pyrimidinyl, pyrazolo[1,5-a]pyrazinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, imidazo[1,2-b]pyridazinyl, purinyl, imidazo[1,2-a]pyrimidinyl, imidazo[1,2-c]-pyrimidinyl, imidazo[1,2-a]pyrazinyl, oxadiazolyl, thiadiazolyl, triazolyl, [1,2,4]triazolo-[1,5-a]pyrimidinyl, 6,8-dihydro-5H-[1,2,4]triazolo[4,3-a]pyrazinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, A represents C—$R^1$. In another embodiment, A represents N.

In one embodiment, B represents C—$R^2$. In another embodiment, B represents N.

In one embodiment, D represents C—$R^3$. In another embodiment, D represents N.

In one embodiment, E represents C—$R^4$. In another embodiment, E represents N.

In a particular embodiment, A represents C—$R^1$, B represents C—$R^2$, D represents C—$R^3$ and E represents C—$R^4$.

Suitably, the present invention provides a compound of formula (I-1) or an N-oxide thereof, or a pharmaceutically acceptable salt thereof:

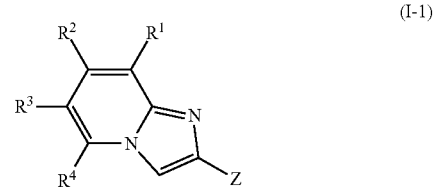

(I-1)

wherein Z, $R^1$, $R^2$, $R^3$ and $R^4$ are as defined above.

Generally, $R^1$, $R^2$, $R^3$ and $R^4$ independently represent hydrogen, halogen, cyano, —$OR^a$, —$SOR^a$, —$NR^bR^c$, —$NR^cCOR^d$ or —N=S(O)$R^bR^c$; or $C_{1-6}$ alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents.

Appositely, $R^1$, $R^2$, $R^3$ and $R^4$ independently represent hydrogen or halogen; or $C_{1-6}$ alkyl or $C_{3-7}$ heterocycloalkenyl, either of which groups may be optionally substituted by one or more substituents.

Suitably, $R^1$, $R^2$, $R^3$ and $R^4$ independently represent hydrogen; or $C_{3-7}$ heterocycloalkenyl, which group may be optionally substituted by one or more substituents.

Aptly, $R^1$, $R^2$, $R^3$ and $R^4$ independently represent hydrogen, fluoro, chloro, cyano, —$OR^a$, —$SOR^a$, —$NR^bR^c$, —$NR^cCOR^d$ or —N=$S(O)R^bR^c$; or methyl, ethyl, propyl, phenyl, benzyl, tetrahydrofuranyl, pyrrolidinyl, tetrahydropyranyl, piperidinyl, piperazinyl, morpholinyl, oxazepinyl, pyrrolidinylmethyl, piperidinylmethyl, piperazinylmethyl, morpholinylmethyl, 2,5-dihydropyrrolyl, 3,6-dihydro-2H-pyranyl, 1,2,3,4-tetrahydropyridinyl, 2,3-dihydro-1,4-oxazinyl, 6,7-dihydro-5H-1,4-oxazepinyl, furyl, pyrazolyl, 6,8-dihydro-5H-[1,2,4]triazolo[4,3-a]pyrazinyl, pyridinyl, pyrimidinyl, pyrazinyl, pyridinylmethyl or pyridinylethyl, any of which groups may be optionally substituted by one or more substituents.

More particularly, $R^1$, $R^2$, $R^3$ and $R^4$ independently represent hydrogen or fluoro; or propyl or 2,5-dihydropyrrolyl, either of which groups may be optionally substituted by one or more substituents.

Typically, $R^1$, $R^2$, $R^3$ and $R^4$ independently represent hydrogen; or 2,5-dihydropyrrolyl, which group may be optionally substituted by one or more substituents.

Illustrative examples of optional substituents which may be present on $R^1$, $R^2$, $R^3$ or $R^4$ include one, two or three substituents independently selected from halogen, cyano, nitro, $C_{1-6}$ alkyl, trifluoromethyl, difluoroethyl, phenyl, fluorophenyl, oxetanyl, pyrrolidinyl, tetrahydropyranyl, morpholinyl, piperazinyl, oxadiazolyl, ($C_{1-6}$)alkyloxadiazolyl, hydroxy, hydroxy($C_{1-6}$)alkyl, oxo, $C_{1-6}$ alkoxy, difluoromethoxy, trifluoromethoxy, pentafluorothio, $C_{1-6}$ alkylthio, $C_{1-6}$ alkylsulfinyl, ($C_{1-6}$)alkyl(imino)sulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkylaminocarbonyl, chloro($C_{1-6}$)alkylaminocarbonyl, di($C_{1-6}$)alkylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)-(methyl)azetidinylcarbonyl, morpholinylcarbonyl, ($C_{1-6}$)alkylpyrazolylcarbonyl, aminosulfonyl, $C_{1-6}$ alkylaminosulfonyl, di($C_{1-6}$)alkylaminosulfonyl, ($C_{1-6}$)alkylsulfoximinyl, trifluoromethylsulfoximinyl, [($C_{1-6}$)alkyl][N—($C_{1-6}$)alkyl]sulfoximinyl, [($C_{1-6}$)alkyl][N-carboxy($C_{1-6}$)alkyl]sulfoximinyl, [N—($C_{2-6}$)alkoxycarbonyl($C_{1-6}$)alkyl][($C_{1-6}$)alkyl]-sulfoximinyl, ($C_{3-7}$)cycloalkylsulfoximinyl, N-[di($C_{1-6}$)alkylsulfoxo]iminyl and di($C_{1-6}$)alkylsulfoximinyl. Additional examples include trifluoroethylaminocarbonyl.

Suitable examples of optional substituents which may be present on $R^1$, $R^2$, $R^3$ or $R^4$ include one, two or three substituents independently selected from halogen, $C_{2-6}$ alkoxycarbonyl, trifluoroethylaminocarbonyl and difluoroazetidinylcarbonyl.

Typical examples of optional substituents which may be present on $R^1$, $R^2$, $R^3$ or $R^4$ include one, two or three substituents independently selected from $C_{2-6}$ alkoxycarbonyl and difluoroazetidinylcarbonyl.

Illustrative examples of particular substituents which may be present on $R^1$, $R^2$, $R^3$ or $R^4$ include one, two or three substituents independently selected from fluoro, chloro, bromo, cyano, nitro, methyl, ethyl, isopropyl, tert-butyl, trifluoromethyl, difluoroethyl, phenyl, fluorophenyl, oxetanyl, pyrrolidinyl, tetrahydropyranyl, morpholinyl, piperazinyl, oxadiazolyl, methyloxadiazolyl, hydroxy, hydroxymethyl, hydroxyisopropyl, oxo, methoxy, tert-butoxy, difluoromethoxy, trifluoromethoxy, pentafluorothio, methylthio, methylsulfinyl, (imino)(methyl)sulfinyl, methylsulfonyl, amino, aminomethyl, aminoethyl, methylamino, tert-butylamino, dimethylamino, acetylamino, acetylaminoethyl, methoxycarbonylamino, methylsulfonylamino, formyl, acetyl, hydroxyacetyl, carboxy, methoxycarbonyl, ethoxycarbonyl, tert-butoxycarbonyl, aminocarbonyl, methylaminocarbonyl, ethylaminocarbonyl, chloropropylaminocarbonyl, dimethylaminocarbonyl, azetidinylcarbonyl, hydroxyazetidinylcarbonyl, difluoroazetidinylcarbonyl, (hydroxy)-(trifluoromethyl)azetidinylcarbonyl, (hydroxy)(methyl)azetidinylcarbonyl, morpholinylcarbonyl, ethylpyrazolylcarbonyl, aminosulfonyl, methylaminosulfonyl, dimethylaminosulfonyl, methylsulfoximinyl, ethylsulfoximinyl, trifluoromethylsulfoximinyl, (methyl)-(N-methyl)sulfoximinyl, (N-carboxymethyl)(methyl)sulfoximinyl, (N-tert-butoxy-carbonylmethyl)(methyl)sulfoximinyl, cyclopropylsulfoximinyl, N-(dimethylsulfoxo)iminyl and dimethylsulfoximinyl. Additional examples include trifluoroethylaminocarbonyl.

Suitable examples of particular substituents which may be present on $R^1$, $R^2$, $R^3$ or $R^4$ include one, two or three substituents independently selected from fluoro, tert-butoxycarbonyl, trifluoroethylaminocarbonyl and difluoroazetidinylcarbonyl.

Typical examples of particular substituents on $R^1$, $R^2$, $R^3$ or $R^4$ include one, two or three substituents independently selected from tert-butoxycarbonyl and difluoroazetidinylcarbonyl.

Particular values of $R^1$, $R^2$, $R^3$ or $R^4$ include hydrogen, fluoro, chloro, cyano, —$OR^a$, —$SOR^a$, —$NR^bR^c$, —$NR^cCOR^d$, —N=$S(O)R^bR^c$, tert-butoxycarbonylmethyl, dimethylaminocarbonylmethyl, acetylaminoethyl, carboxyethyl, tert-butoxycarbonylethyl, methylaminocarbonylethyl, dimethylaminocarbonylethyl, acetylaminopropyl, methylsulfonylphenyl, methylsulfonylaminophenyl, tert-butoxycarbonylphenyl, dimethylaminocarbonylphenyl, ethoxycarbonylbenzyl, carboxytetrahydrofuranyl, methoxycarbonyltetrahydrofuranyl, dimethylaminocarbonyltetrahydrofuranyl, hydroxyazetidinylcarbonyltetrahydrofuranyl, difluoroazetidinylcarbonyltetrahydrofuranyl, (hydroxy)(trifluoromethyl)-azetidinylcarbonyltetrahydrofuranyl, morpholinylcarbonyltetrahydrofuranyl, methoxycarbonylpyrrolidinyl, tert-butoxycarbonylpyrrolidinyl, dimethylaminocarbonylpyrrolidinyl, difluoroazetidinylcarbonylpyrrolidinyl, (ethoxycarbonyl)(methylsulfonyl)-pyrrolidinyl, (acetyl)(ethoxycarbonyl)pyrrolidinyl, (tert-butoxycarbonyl)(difluoroazetidinylcarbonyl)pyrrolidinyl, tetrahydropyranyl, ethoxycarbonyltetrahydropyranyl, dimethylaminocarbonyltetrahydropyranyl, piperidinyl, methylpiperidinyl, acetylpiperidinyl, hydroxyacetylpiperidinyl, methoxycarbonylpiperidinyl, tert-butoxycarbonylpiperidinyl, dimethylaminocarbonylpiperidinyl, ethylpyrazolylcarbonylpiperidinyl, methylpiperazinyl, morpholinyl, methyloxadiazolylmorpholinyl, methylsulfonylmorpholinyl, acetylmorpholinyl, hydroxyacetylmorpholinyl, methoxycarbonylmorpholinyl, ethoxycarbonylmorpholinyl, tert-butoxycarbonylmorpholinyl, ethylaminocarbonylmorpholinyl, difluoroazetidinylcarbonylmorpholinyl, oxazepinyl, tert-butoxycarbonyloxazepinyl, oxopyrrolidinylmethyl, carboxypyrrolidinylmethyl, methoxycarbonylpyrrolidinylmethyl, dimethylaminocarbonylpyrrolidinylmethyl, methylsulfonylpiperidinylmethyl, piperazinylmethyl, methylpiperazinylmethyl, oxetanylpiperazinylmethyl, methylsulfonylpiperazinylmethyl, acetylpiperazinylmethyl, tert-butoxycarbonylpiperazinylmethyl, (acetyl)(tert-butoxycarbonyl)piperazinylmethyl, morpholinylmethyl, (tert-butoxycarbonyl)(difluoroazetidinylcarbonyl)-2,5-dihydropyrrolyl, 3,6-dihydro-2H-pyranyl, ethoxycarbonyl-3,6-dihydro-2H-pyranyl, dimethylaminocarbonyl-3,6-dihydro-2H-pyranyl, tert-butoxycarbonyl-1,2,3,4-tetrahydropyridinyl, tert-butoxycarbonyl-2,3-dihydro-1,4-oxazinyl, tert-butoxycarbonyl-6,7-dihydro-5H-1,4-oxazepinyl, difluoroazetidinylcarbonylfuryl, difluoroazetidinylcarbonylpyrazolyl, acetyl-6,8-dihydro-5H-[1,2,4]triazolo[4,3-a]pyrazinyl, (imino)(methyl)sulfinylpyridinyl, ethoxycarbonylpyridinyl, chloropropylaminocarbonylpyridinyl, dimethylaminocarbonylpyridinyl, azetidinylcarbonylpyridinyl, difluoroazetidinylcarbonylpyridinyl, (hydroxy)(methyl)-azetidinylcarbonylpyridinyl, (dimethylaminocarbonyl)(fluoro)pyridinyl, dimethylaminocarbonylpyrimidinyl, (dimethylaminocarbonyl)(methyl)pyrimidinyl, dimethylaminocarbonylpyrazinyl, pyridinylmethyl, cyanopyridinylmethyl, oxadiazolylpyridinylmethyl, ethoxycarbonylpyridinylmethyl, aminocarbonylpyridinylmethyl, pyridinylethyl and hydroxypyridinylethyl. Additional values include (difluoro)(trifluoroethylaminocarbonyl)propyl.

Selected values of $R^1$, $R^2$, $R^3$ or $R^4$ include hydrogen, fluoro, (difluoro)(trifluoroethylaminocarbonyl)propyl and (tert-butoxycarbonyl)(difluoroazetidinylcarbonyl)-2,5-dihydropyrrolyl.

Suitable values of $R^1$, $R^2$, $R^3$ or $R^4$ include hydrogen and (tert-butoxycarbonyl)-(difluoroazetidinylcarbonyl)-2,5-dihydropyrrolyl.

Suitably, $R^1$ represents hydrogen, halogen, cyano or —$OR^a$.

Appositely, $R^1$ represents hydrogen or halogen.

In a first embodiment, $R^1$ represents hydrogen. In a second embodiment, $R^1$ represents halogen. In one aspect of that embodiment, $R^1$ represents fluoro. In another aspect of that embodiment, $R^1$ represents chloro. In a third embodiment, $R^1$ represents cyano. In a fourth embodiment, $R^1$ represents —$OR^a$.

Illustrative values of $R^1$ include hydrogen, fluoro, chloro, cyano and —$OR^a$.

Selected values of $R^1$ include hydrogen and fluoro.

Generally, $R^2$ represents hydrogen, cyano, —$OR^a$, —$SOR^a$, —$NR^bR^c$, —$NR^cCOR^d$ or —N=S(O)$R^bR^c$; or $R^2$ represents $C_{1-6}$ alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents.

Appositely, $R^2$ represents $C_{1-6}$ alkyl or $C_{3-7}$ heterocycloalkenyl, either of which groups may be optionally substituted by one or more substituents.

Suitably, $R^2$ represents $C_{3-7}$ heterocycloalkenyl, which group may be optionally substituted by one or more substituents.

Aptly, $R^2$ represents hydrogen, cyano, —$OR^a$, —$SOR^a$, —$NR^bR^c$, —$NR^cCOR^d$ or —N=S(O)$R^bR^c$; or $R^2$ represents methyl, ethyl, propyl, phenyl, benzyl, tetrahydrofuranyl, pyrrolidinyl, tetrahydropyranyl, piperidinyl, piperazinyl, morpholinyl, oxazepinyl, pyrrolidinylmethyl, piperidinylmethyl, piperazinylmethyl, morpholinylmethyl, 2,5-dihydropyrrolyl, 3,6-dihydro-2H-pyranyl, 1,2,3,4-tetrahydropyridinyl, 2,3-dihydro-1,4-oxazinyl, 6,7-dihydro-5H-1,4-oxazepinyl, furyl, pyrazolyl, 6,8-dihydro-5H-[1,2,4]-triazolo[4,3-a]pyrazinyl, pyridinyl, pyrimidinyl, pyrazinyl, pyridinylmethyl or pyridinylethyl, any of which groups may be optionally substituted by one or more substituents.

More particularly, $R^2$ represents propyl or 2,5-dihydropyrrolyl, either of which groups may be optionally substituted by one or more substituents.

Typically, $R^2$ represents 2,5-dihydropyrrolyl, which group may be optionally substituted by one or more substituents.

Illustrative examples of optional substituents on $R^2$ include one, two or three substituents independently selected from halogen, cyano, nitro, $C_{1-6}$ alkyl, trifluoromethyl, phenyl, fluorophenyl, oxetanyl, pyrrolidinyl, tetrahydropyranyl, morpholinyl, piperazinyl, oxadiazolyl, ($C_{1-6}$)alkyloxadiazolyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, ($C_{1-6}$)alkyl-(imino)sulfinyl, $C_{1-6}$ alkylsulfonyl, amino, amino($C_{1-6}$)alkyl, $C_{1-6}$ alkylamino, di($C_{1-6}$)-alkylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkylaminocarbonyl, chloro-($C_{1-6}$)alkylaminocarbonyl, di($C_{1-6}$) alkylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)(methyl)azetidinylcarbonyl, morpholinylcarbonyl, ($C_{1-6}$)alkylpyrazolylcarbonyl, aminosulfonyl, $C_{1-6}$ alkylaminosulfonyl, di($C_{1-6}$)alkylaminosulfonyl and di($C_{1-6}$)alkylsulfoximinyl. Additional examples include trifluoro-ethylaminocarbonyl.

Suitable examples of optional substituents on $R^2$ include one, two or three substituents independently selected from halogen, $C_{2-6}$ alkoxycarbonyl, trifluoroethylaminocarbonyl and difluoroazetidinylcarbonyl.

Typical examples of optional substituents on $R^2$ include one, two or three substituents independently selected from $C_{2-6}$ alkoxycarbonyl and difluoroazetidinylcarbonyl.

Illustrative examples of particular substituents on $R^2$ include one, two or three substituents independently selected from fluoro, chloro, bromo, cyano, nitro, methyl, ethyl, isopropyl, tert-butyl, trifluoromethyl, phenyl, fluorophenyl, oxetanyl, pyrrolidinyl, tetrahydropyranyl, morpholinyl, piperazinyl, oxadiazolyl, methyloxadiazolyl, hydroxy, hydroxymethyl, oxo, methoxy, tert-butoxy, difluoromethoxy, trifluoromethoxy, methylthio, methylsulfinyl, (imino)(methyl)sulfinyl, methylsulfonyl, amino, aminomethyl, aminoethyl, methylamino, tert-butylamino, dimethylamino, acetamino, acetylaminoethyl, methoxycarbonylamino, methylsulfonylamino, formyl, acetyl, hydroxyacetyl, carboxy, methoxycarbonyl, ethoxycarbonyl, tert-butoxycarbonyl, aminocarbonyl, methylaminocarbonyl, ethylaminocarbonyl, chloropropylaminocarbonyl, dimethylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)(methyl)azetidinylcarbonyl, morpholinylcarbonyl, ethylpyrazolylcarbonyl, aminosulfonyl, methylaminosulfonyl, dimethylaminosulfonyl and dimethylsulfoximinyl. Additional examples include trifluoro-ethylaminocarbonyl.

Suitable examples of particular substituents on $R^2$ include one, two or three substituents independently selected from fluoro, tert-butoxycarbonyl, trifluoroethylaminocarbonyl and difluoroazetidinylcarbonyl.

Typical examples of particular substituents on $R^2$ include one, two or three substituents independently selected from tert-butoxycarbonyl and difluoroazetidinylcarbonyl.

Illustrative values of $R^2$ include hydrogen, cyano, —$OR^a$, —$SOR^a$, —$NR^bR^c$, —$NR^cCOR^d$, —N=S(O)$R^bR^c$, tert-butoxycarbonylmethyl, dimethylaminocarbonylmethyl, acetylaminoethyl, carboxyethyl, tert-butoxycarbonylethyl, methylaminocarbonylethyl, dimethylaminocarbonylethyl, acetylaminopropyl, methylsulfonylphenyl, methylsulfonylaminophenyl, tert-butoxycarbonylphenyl, dimethylaminocarbonylphenyl, ethoxycarbonylbenzyl, carboxytetrahydrofuranyl, methoxycarbonyltetrahydrofuranyl, dimethylaminocarbonyltetrahydrofuranyl, hydroxyazetidinylcarbonyltetrahydrofuranyl, difluoroazetidinylcarbonyltetrahydrofuranyl, (hydroxy)(trifluoromethyl)azetidinylcarbonyltetrahydrofuranyl, morpholinylcarbonyltetrahydrofuranyl, methoxycarbonylpyrrolidinyl, tert-butoxycarbonylpyrrolidinyl, dimethylaminocarbonylpyrrolidinyl, difluoroazetidinylcarbonylpyrrolidinyl, (ethoxycarbonyl)(methylsulfonyl)pyrrolidinyl, (acetyl)-(ethoxycarbonyl)pyrrolidinyl, (tert-butoxycarbonyl)(difluoroazetidinylcarbonyl)-pyrrolidinyl, tetrahydropyranyl, ethoxycarbonyltetrahydropyranyl, dimethylaminocarbonyltetrahydropyranyl, piperidinyl, methylpiperidinyl, acetylpiperidinyl, hydroxyacetylpiperidinyl, methoxycarbonylpiperidinyl, tert-butoxycarbonylpiperidinyl, dimethylaminocarbonylpiperidinyl, ethylpyrazolylcarbonylpiperidinyl, methylpiperazinyl, morpholinyl, methyloxadiazolylmorpholinyl, methylsulfonylmorpholinyl, acetylmorpholinyl, hydroxyacetylmorpholinyl, methoxycarbonylmorpholinyl, ethoxycarbonylmorpholinyl, tert-butoxycarbonylmorpholinyl, ethylaminocarbonylmorpholinyl, difluoroazetidinylcarbonylmorpholinyl, oxazepinyl, tert-butoxycarbonyloxazepinyl, oxopyrrolidinylmethyl, carboxypyrrolidinylmethyl, methoxycarbonylpyrrolidinylmethyl, dimethylaminocarbonylpyrrolidinylmethyl, methylsulfonylpiperidinylmethyl, piperazinylmethyl, methylpiperazinylmethyl, oxetanylpiperazinylmethyl, methylsulfonylpiperazinylmethyl, acetylpiperazinylmethyl, tert-butoxycarbonylpiperazinylmethyl, (acetyl)(tert-butoxycarbonyl)piperazinylmethyl, morpholinylmethyl, (tert-butoxy-carbonyl)(difluoroazetidinylcarbonyl)-2,5-dihydropyrrolyl, 3,6-dihydro-2H-pyranyl, ethoxycarbonyl-3,6-dihydro-2H-pyranyl, dimethylaminocarbonyl-3,6-dihydro-2H-pyranyl, tert-butoxycarbonyl-1,2,3,4-tetrahydropyridinyl, tert-butoxycarbonyl-2,3-dihydro-1,4-oxazinyl, tert-butoxycarbonyl-6,7-dihydro-5H-1,4-oxazepinyl, difluoroazetidinylcarbonylfuryl, difluoroazetidinylcarbonylpyrazolyl, acetyl-6,8-dihydro-5H-[1,2,4]triazolo[4,3-a]pyrazinyl, (imino)(methyl)sulfinylpyridinyl, ethoxycarbonylpyridinyl, chloropropylaminocarbonylpyridinyl, dimethylaminocarbonylpyridinyl, azetidinylcarbonylpyridinyl, difluoroazetidinylcarbonylpyridinyl, (hydroxy)(methyl)-azetidinylcarbonylpyridinyl, (dimethylaminocarbonyl)(fluoro)pyridinyl, dimethylaminocarbonylpyrimidinyl, (dimethylaminocarbonyl)(methyl)pyrimidinyl, dimethylaminocarbonylpyrazinyl, pyridinylmethyl, cyanopyridinylmethyl, oxadiazolylpyridinylmethyl, ethoxycarbonylpyridinylmethyl, aminocarbonylpyridinylmethyl, pyridinylethyl and hydroxypyridinylethyl. Additional values include (difluoro)(trifluoroethylaminocarbonyl)propyl.

Selected values of $R^2$ include (difluoro)(trifluoroethylaminocarbonyl)propyl and (tert-butoxycarbonyl)(difluoroazetidinylcarbonyl)-2,5-dihydropyrrolyl.

Suitable values of $R^2$ include (tert-butoxycarbonyl)(difluoroazetidinylcarbonyl)-2,5-dihydropyrrolyl.

Typically, $R^3$ represents hydrogen, halogen or —$NR^bR^c$; or $R^3$ represents $C_{1-6}$ alkyl, aryl, $C_{3-7}$ heterocycloalkyl, $C_{3-7}$ heterocycloalkyl($C_{1-6}$)alkyl or heteroaryl, any of which groups may be optionally substituted by one or more substituents.

Suitably, $R^3$ represents hydrogen, fluoro or —$NR^bR^c$; or $R^3$ represents ethyl, phenyl, morpholinyl, piperidinylmethyl, piperazinylmethyl, morpholinylmethyl or pyridinyl, any of which groups may be optionally substituted by one or more substituents.

Typical examples of optional substituents on $R^3$ include one, two or three substituents independently selected from halogen, cyano, nitro, $C_{1-6}$ alkyl, trifluoromethyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, difluoroazetidinylcarbonyl, aminosulfonyl, $C_{1-6}$ alkylaminosulfonyl and di($C_{1-6}$)alkylaminosulfonyl.

Typical examples of particular substituents on $R^3$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, difluoroazetidinylcarbonyl, aminosulfonyl, methylaminosulfonyl and dimethylaminosulfonyl.

Illustrative values of $R^3$ include hydrogen, fluoro, —$NR^bR^c$, tert-butoxycarbonylethyl, dimethylaminocarbonylphenyl, morpholinyl, methylsulfonylpiperidinylmethyl, methylsulfonylpiperazinylmethyl, acetylpiperazinylmethyl, morpholinylmethyl and difluoroazetidinylcarbonylpyridinyl.

In a particular embodiment, $R^3$ represents hydrogen.

Typically, $R^4$ represents hydrogen, halogen or —$OR^a$.

In a first embodiment, $R^4$ represents hydrogen. In a second embodiment, $R^4$ represents halogen. In one aspect of that embodiment, $R^4$ represents fluoro. In another aspect of that embodiment, $R^4$ represents chloro. In a third embodiment, $R^4$ represents —$OR^a$.

Typical values of $R^4$ include hydrogen, fluoro and —$OR^a$, especially hydrogen.

In a first embodiment, Z represents —$CH(R^5)N(H)C(O)R^6$.

In a second embodiment, Z represents —$CH(R^5)N(H)S(O)_2R^6$.

In a third embodiment, Z represents —$C(=CR^{5a}R^{5b})N(H)C(O)R^6$.

In a fourth embodiment, Z represents —$CH(R^5)R^7$.

In a fifth embodiment, Z represents —$CH(R^5)N(H)R^7$.

In a sixth embodiment, Z represents —$CH(R^5)C(O)N(H)R^7$.

A first sub-class of compounds according to the invention is represented by the compounds of formula (IA), and pharmaceutically acceptable salts thereof:

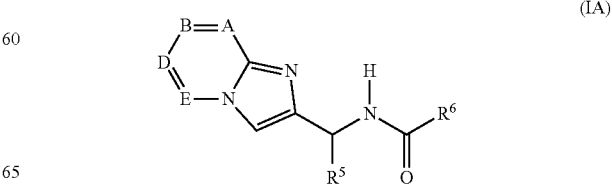

(IA)

wherein
A, B, D, E, $R^5$ and $R^6$ are as defined above.

A second sub-class of compounds according to the invention is represented by the compounds of formula (IB), and pharmaceutically acceptable salts thereof:

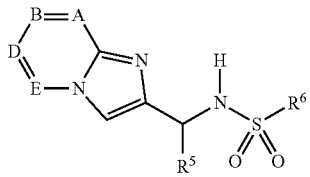

(IB)

wherein
A, B, D, E, $R^5$ and $R^6$ are as defined above.

A third sub-class of compounds according to the invention is represented by the compounds of formula (IC), and pharmaceutically acceptable salts thereof:

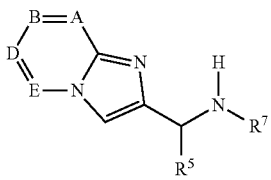

(IC)

wherein
A, B, D, E, $R^5$ and $R^7$ are as defined above.

A fourth sub-class of compounds according to the invention is represented by the compounds of formula (ID), and pharmaceutically acceptable salts thereof:

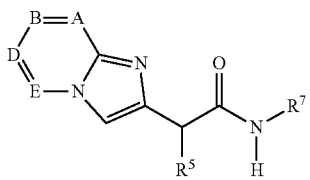

(ID)

wherein
A, B, D, E, $R^5$ and $R^7$ are as defined above.

A fifth sub-class of compounds according to the invention is represented by the compounds of formula (IE), and pharmaceutically acceptable salts thereof:

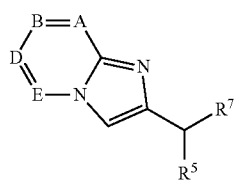

(IE)

wherein
A, B, D, E, $R^5$ and $R^7$ are as defined above.

A sixth sub-class of compounds according to the invention is represented by the compounds of formula (IF), and pharmaceutically acceptable salts thereof:

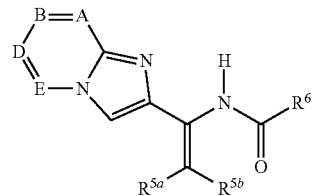

(IF)

wherein
A, B, D, E, $R^{5a}$, $R^{5b}$ and $R^6$ are as defined above.

Generally, Z represents —CH($R^5$)N(H)C(O)$R^6$.

Thus, a particular sub-class of compounds according to the invention is represented by the compounds of formula (IA) as defined above, and pharmaceutically acceptable salts thereof.

Typically, $R^5$ represents $C_{1-6}$ alkyl, $C_{3-9}$ cycloalkyl, $C_{3-9}$ cycloalkyl($C_{1-6}$)alkyl, $C_{4-9}$ cycloalkenyl, $C_{4-12}$ bicycloalkyl, $C_{5-9}$ spirocycloalkyl, $C_{5-9}$ spirocycloalkyl($C_{1-5}$)alkyl, $C_8$-11 tricycloalkyl, $C_8$-11 tricycloalkyl($C_{1-6}$)alkyl, $C_7$-13 dispirocycloalkyl, aryl, aryl-($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Suitably, $R^5$ represents $C_{3-9}$ cycloalkyl, $C_{4-12}$ bicycloalkyl, $C_{5-9}$ spirocycloalkyl or $C_7$-13 dispirocycloalkyl, any of which groups may be optionally substituted by one or more substituents.

Appositely, $R^5$ represents $C_{3-9}$ cycloalkyl, which group may be optionally substituted by one or more substituents.

In a first embodiment, $R^5$ represents hydrogen. In a second embodiment, $R^5$ represents optionally substituted $C_{1-6}$ alkyl. In a third embodiment, $R^5$ represents optionally substituted $C_{3-9}$ cycloalkyl. In a fourth embodiment, $R^5$ represents optionally substituted $C_{3-9}$ cycloalkyl($C_{1-6}$)alkyl. In a fifth embodiment, $R^5$ represents optionally substituted $C_{4-9}$ cycloalkenyl. In a sixth embodiment, $R^5$ represents optionally substituted $C_{4-9}$ bicycloalkyl. In a seventh embodiment, $R^5$ represents optionally substituted $C_{5-9}$ spirocycloalkyl. In an eighth embodiment, $R^5$ represents optionally substituted $C_{5-9}$ spirocycloalkyl($C_{1-6}$)alkyl. In a ninth embodiment, $R^5$ represents optionally substituted $C_{8-11}$ tricycloalkyl. In a tenth embodiment, $R^5$ represents optionally substituted $C_{8-11}$ tricycloalkyl($C_{1-6}$)alkyl. In an eleventh embodiment, $R^5$ represents optionally substituted aryl. In a twelfth embodiment, $R^5$ represents optionally substituted aryl($C_{1-6}$)alkyl. In a thirteenth embodiment, $R^5$ represents optionally substituted $C_{3-7}$ heterocycloalkyl. In a fourteenth embodiment, $R^5$ represents optionally substituted $C_{3-7}$ heterocycloalkyl($C_{1-6}$)-alkyl. In a fifteenth embodiment, $R^5$ represents optionally substituted heteroaryl. In a sixteenth embodiment, $R^5$ represents optionally substituted heteroaryl($C_{1-6}$)alkyl. In a seventeenth embodiment, $R^5$ represents optionally substituted $C_7$-13 dispirocycloalkyl. In an eighteenth embodiment, $R^5$ represents optionally substituted $C_7$-13 dispirocycloalkyl-($C_{1-6}$)alkyl.

In a particular embodiment, $R^5$ is other than hydrogen.

Typical values of $R^5$ include methyl, isopropyl, 1-methylpropyl, 2-methylpropyl, cyclopropyl, cyclopentyl, indanyl, cyclohexyl, cycloheptyl, cyclooctyl, cyclohexylmethyl, cyclooctenyl, bicyclo[4.1.0]heptanyl, spiro[3.3]heptanyl, spiro[2.5]octanyl, spiro[3.3]-heptanylmethyl, adamantanyl, adamantanylmethyl, dispiro[2.0.24.13]heptanyl, phenyl, benzyl, phenylethyl, naphthylmethyl, thienyl, indolyl, pyridinyl, thienylmethyl, indolylmethyl and pyridinylmethyl, any of which groups may be optionally substituted by one or more substituents.

Illustrative values of $R^5$ include cyclopentyl, cyclohexyl, cycloheptyl, cyclooctyl, bicyclo[4.1.0]heptanyl, spiro[2.5]octanyl and dispiro[2.0.24.13]heptanyl, any of which groups may be optionally substituted by one or more substituents.

Suitable values of $R^5$ include cyclohexyl and cyclooctyl, either of which groups may be optionally substituted by one or more substituents.

Apposite values of $R^5$ include cyclohexyl, which group may be optionally substituted by one or more substituents.

Typical examples of optional substituents on $R^5$ include one, two or three substituents independently selected from halogen, cyano, nitro, $C_{1-6}$ alkyl, trifluoromethyl, phenyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^5$ include one, two or three substituents independently selected from halogen, cyano, $C_{1-6}$ alkyl, trifluoromethyl, phenyl, hydroxy, $C_{1-6}$ alkoxy and aminocarbonyl, especially $C_{1-6}$ alkyl.

Selected examples of optional substituents on $R^5$ include one, two or three substituents independently selected from halogen and $C_{1-6}$ alkyl, especially $C_{1-6}$ alkyl.

Typical examples of particular substituents on $R^5$ include one, two or three substituents independently selected from fluoro, chloro, bromo, cyano, nitro, methyl, ethyl, isopropyl, tert-butyl, trifluoromethyl, phenyl, hydroxy, oxo, methoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Suitable examples of particular substituents on $R^5$ include one, two or three substituents independently selected from fluoro, chloro, bromo, cyano, methyl, trifluoromethyl, phenyl, hydroxy, methoxy, tert-butoxy and aminocarbonyl, especially methyl.

Selected examples of particular substituents on $R^5$ include one, two or three substituents independently selected from fluoro and methyl, especially methyl.

Illustrative examples of specific values of $R^5$ include hydrogen, methyl, isopropyl, 1-methylpropyl, 2-methylpropyl, cyclopropyl, cyclopentyl, indanyl, cyclohexyl, methylcyclohexyl, trifluoromethylcyclohexyl, difluorocyclohexyl, dimethylcyclohexyl, cycloheptyl, cyclooctyl, cyclohexylmethyl, cyclooctenyl, bicyclo[4.1.0]heptanyl, spiro-[3.3]heptanyl, spiro[2.5]octanyl, dispiro[2.0.24.13]heptanyl, phenyl, chlorophenyl, benzyl, fluorobenzyl, chlorobenzyl, (chloro)(fluoro)benzyl, dichlorobenzyl, bromobenzyl, cyanobenzyl, methylbenzyl, trifluoromethylbenzyl, phenylbenzyl, hydroxybenzyl, methoxybenzyl, tert-butoxybenzyl, aminocarbonylbenzyl, phenylethyl, chlorophenylethyl, naphthylmethyl, thienylmethyl, indolylmethyl and pyridinylmethyl.

Apposite examples of particular values of $R^5$ include cyclopentyl, cyclohexyl, methylcyclohexyl, difluorocyclohexyl, dimethylcyclohexyl, cycloheptyl, cyclooctyl, bicyclo[4.1.0]heptanyl, spiro[2.5]octanyl and dispiro[2.0.24.13]heptanyl.

Selected examples of particular values of $R^5$ include methylcyclohexyl and difluorocyclohexyl.

Representative examples of specific values of $R^5$ include methylcyclohexyl and cyclooctyl.

In a first embodiment, $R^5$ represents methylcyclohexyl, especially 4-methylcyclohexyl. In a second embodiment, $R^5$ represents difluorocyclohexyl, especially 4,4-difluorocyclohexyl. In a third embodiment, $R^5$ represents cyclooctyl.

In a first embodiment, $R^{5a}$ represents optionally substituted $C_{3-7}$ cycloalkyl. In a second embodiment, $R^{5a}$ represents optionally substituted $C_{4-9}$ bicycloalkyl. In a third embodiment, $R^{5a}$ represents optionally substituted aryl. In a fourth embodiment, $R^{5a}$ represents optionally substituted $C_{3-7}$ heterocycloalkyl. In a fifth embodiment, $R^{5a}$ represents optionally substituted heteroaryl.

Typical values of $R^{5a}$ include cyclobutyl, cyclopentyl, bicyclo[1.1.1]pentanyl, phenyl, dihydrobenzofuranyl and pyrrolyl, any of which groups may be optionally substituted by one or more substituents.

Typical examples of optional substituents on $R^{5a}$ include $C_{1-6}$ alkyl, halogen, cyano, trifluoromethyl, trifluoroethyl, phenyl, hydroxy, $C_{1-6}$ alkoxy, $C_{1-6}$ alkylthio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkylamino.

Selected examples of optional substituents on $R^{5a}$ include $C_{1-6}$ alkyl and halogen. Typical examples of particular substituents on $R^{5a}$ include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Selected examples of particular substituents on $R^{5a}$ include methyl and chloro.

Selected values of $R^{5a}$ include cyclobutyl, cyclopentyl, bicyclo[1.1.1]pentanyl, phenyl, chlorophenyl, dihydrobenzofuranyl and methylpyrrolyl.

Suitably, $R^{5b}$ represents hydrogen, methyl or ethyl.

In a first embodiment, $R^{5b}$ represents hydrogen. In a second embodiment, $R^{5b}$ represents $C_{1-6}$ alkyl, especially methyl or ethyl.

Alternatively, $R^{5a}$ and $R^{5b}$, when taken together with the carbon atom to which they are both attached, may represent $C_{3-7}$ cycloalkyl, $C_{4-9}$ bicycloalkyl or $C_{3-7}$ heterocycloalkyl, any of which groups may be unsubstituted, or substituted by one or more substituents, typically by one or two substituents.

In a first embodiment, $R^{5a}$ and $R^{5b}$, when taken together with the carbon atom to which they are both attached, may suitably represent optionally substituted $C_{3-7}$ cycloalkyl. Examples include cyclobutyl, benzocyclobutenyl, cyclopentyl, indanyl, cyclohexyl, tetrahydronaphthalenyl, cycloheptanyl, benzocycloheptenyl, cyclooctanyl and cyclononanyl, any of which groups may be optionally substituted by one or more substituents.

In a second embodiment, $R^{5a}$ and $R^{5b}$, when taken together with the carbon atom to which they are both attached, may suitably represent optionally substituted $C_{4-9}$ bicycloalkyl. Examples include bicyclo[3.1.0]hexanyl, bicyclo[2.2.1]heptanyl and bicyclo[3.2.1]octanyl, any of which groups may be optionally substituted by one or more substituents.

In a third embodiment, $R^{5a}$ and $R^{5b}$, when taken together with the carbon atom to which they are both attached, may suitably represent optionally substituted $C_{3-7}$ heterocycloalkyl. Examples include tetrahydropyranyl and piperidinyl, either of which groups may be optionally substituted by one or more substituents.

Typical examples of optional substituents on such groups include $C_{1-6}$ alkyl, halogen, cyano, trifluoromethyl, trifluoroethyl, phenyl, hydroxy, $C_{1-6}$ alkoxy, $C_{1-6}$ alkylthio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkylamino.

Selected examples of optional substituents on such groups include $C_{1-6}$ alkyl, halogen, trifluoromethyl, trifluoroethyl, phenyl and $C_{1-6}$ alkoxy.

Typical examples of particular substituents on such groups include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Selected examples of particular substituents on such groups include methyl, chloro, trifluoromethyl, trifluoroethyl, phenyl and methoxy.

Selected values of $R^{5a}$ and $R^{5b}$, when taken together with the carbon atom to which they are both attached, include methylcyclobutyl, dimethylcyclobutyl, phenylcyclobutyl, benzocyclobutenyl, methylbenzocyclobutenyl, chlorobenzocyclobutenyl, methoxy-benzocyclobutenyl, cyclopentyl, methylcyclopentyl, indanyl, chloroindanyl, cyclohexyl, methylcyclohexyl, dimethylcyclohexyl, trifluoromethylcyclohexyl, tetrahydronaphthalenyl, cycloheptanyl, benzocycloheptenyl, cyclooctanyl, cyclononanyl, bicyclo[3.1.0]hexanyl, bicyclo[2.2.1]heptanyl, bicyclo[3.2.1]octanyl, tetramethyl-tetrahydropyranyl and trifluoroethylpiperidinyl.

Typically, $R^6$ represents —$OR^{6a}$ or —$NR^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, heteroaryl or heteroaryl-($C_{1-6}$)alkyl, any of which groups may be optionally substituted by one or more substituents.

Suitably, $R^6$ represents —$OR^{6a}$; or $R^6$ represents $C_{1-6}$ alkyl, aryl or heteroaryl, any of which groups may be optionally substituted by one or more substituents.

Appositely, $R^6$ represents —$OR^{6a}$; or $R^6$ represents heteroaryl, which group may be optionally substituted by one or more substituents.

In a first embodiment, $R^6$ represents optionally substituted $C_{1-6}$ alkyl. In a second embodiment, $R^6$ represents optionally substituted $C_{3-9}$ cycloalkyl. In a third embodiment, $R^6$ represents optionally substituted $C_{3-9}$ cycloalkyl($C_{1-6}$)alkyl. In a fourth embodiment, $R^6$ represents optionally substituted aryl. In a fifth embodiment, $R^6$ represents optionally substituted aryl($C_{1-6}$)alkyl. In a sixth embodiment, $R^6$ represents optionally substituted $C_{3-7}$ heterocycloalkyl. In a seventh embodiment, $R^6$ represents optionally substituted $C_{3-7}$ heterocycloalkyl($C_{1-6}$)alkyl. In an eighth embodiment, $R^6$ represents optionally substituted heteroaryl. In a ninth embodiment, $R^6$ represents optionally substituted heteroaryl($C_{1-6}$)alkyl. In a tenth embodiment, $R^6$ represents —$OR^{6a}$. In an eleventh embodiment, $R^6$ represents —$NR^{6a}R^{6b}$.

Typical values of $R^6$ include —$OR^{6a}$ or —$NR^{6a}R^{6b}$; and methyl, ethyl, propyl, 2-methylpropyl, butyl, cyclopropyl, cyclobutyl, cyclohexyl, cyclohexylmethyl, phenyl, benzyl, phenylethyl, pyrazolyl, isoxazolyl, oxadiazolyl, pyridinyl, triazolylmethyl, benzotriazolylmethyl or pyridinylmethyl, any of which groups may be optionally substituted by one or more substituents.

Illustrative values of $R^6$ include —$OR^{6a}$; and methyl, phenyl, pyrazolyl, isoxazolyl or oxadiazolyl, any of which groups may be optionally substituted by one or more substituents.

Suitable values of $R^6$ include pyrazolyl, isoxazolyl and oxadiazolyl, any of which groups may be optionally substituted by one or more substituents.

Particular values of $R^6$ include oxadiazolyl, which group may be optionally substituted by one or more substituents.

Typical examples of optional substituents on $R^6$ include one, two or three substituents independently selected from halogen, cyano, nitro, $C_{1-6}$ alkyl, trifluoromethyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, pyrrolidinyl, tetrahydropyranyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl and di-($C_{1-6}$)alkylsulfoximinyl.

Suitable examples of optional substituents on $R^6$ include one, two or three substituents independently selected from $C_{1-6}$ alkyl.

Typical examples of particular substituents on $R^6$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, tetrahydropyranyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl, dimethylaminosulfonyl and dimethylsulfoximinyl.

Selected examples of particular substituents on $R^6$ include one, two or three substituents independently selected from methyl and ethyl.

Suitable examples of particular substituents on $R^6$ include one, two or three substituents independently selected from methyl.

Illustrative examples of particular values of $R^6$ include methyl, difluoromethyl, methylsulfonylmethyl, aminomethyl, methylaminomethyl, difluoroethyl, carboxyethyl, difluoropropyl, 2-methylpropyl, butyl, cyanocyclopropyl, methylcyclopropyl, ethyl-cyclopropyl, dimethylcyclopropyl, trifluoromethylcyclopropyl, phenylcyclopropyl, fluorophenylcyclopropyl, hydroxycyclopropyl, aminocyclopropyl, cyclobutyl, trifluoromethylcyclobutyl, cyclohexyl, cyclohexylmethyl, phenyl, fluorophenyl, chlorophenyl, cyanophenyl, methylphenyl, hydroxyphenyl, methylsulfonylphenyl, dimethyl-sulfoximinylphenyl, benzyl, fluorobenzyl, difluorobenzyl, chlorobenzyl, (chloro)(fluoro)benzyl, dichlorobenzyl, (chloro)(difluoro)benzyl, bromobenzyl, cyanobenzyl, methylbenzyl, dimethylbenzyl, trifluoromethylbenzyl, phenylbenzyl, hydroxybenzyl, hydroxymethylbenzyl, benzoyl, methoxybenzyl, dimethoxybenzyl, trifluoromethoxy-benzyl, methylsulfonylbenzyl, aminomethylbenzyl, aminoethylbenzyl, dimethylaminobenzyl, pyrrolidinylbenzyl, (dimethyl)(pyrrolidinyl)benzyl, morpholinylbenzyl, (dimethyl)(morpholinyl)benzyl, piperazinylbenzyl, acetylaminoethylbenzyl, phenylethyl, chlorophenylethyl, methylpyrazolyl, ethylpyrazolyl, (methyl)(tetrahydropyranyl)pyrazolyl, methylisoxazolyl, ethylisoxazolyl, methyloxadiazolyl, ethyloxadiazolyl, pyridinyl, triazolylmethyl, benzotriazolylmethyl, pyridinylmethyl and aminopyridinylmethyl.

Favoured values of $R^6$ include methylpyrazolyl, ethylpyrazolyl, methylisoxazolyl, ethylisoxazolyl, methyloxadiazolyl and ethyloxadiazolyl.

Selected values of $R^6$ include methyloxadiazolyl and ethyloxadiazolyl.

A particular value of $R^6$ is methyloxadiazolyl.

Generally, $R^{6a}$ represents $C_{1-6}$ alkyl.

In a first embodiment, $R^{6a}$ represents $C_{1-6}$ alkyl. In a second embodiment, $R^{6a}$ represents optionally substituted $C_{3-9}$ cycloalkyl.

Typically, $R^{6a}$ represents $C_{1-6}$ alkyl; or $R^{6a}$ represents cyclobutyl, which group may be optionally substituted by one or more substituents.

Typical examples of optional substituents on $R^{6a}$ include one, two or three substituents independently selected from halogen, cyano, nitro, $C_{1-6}$ alkyl, trifluoromethyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^{6a}$ include one, two or three substituents independently selected from halogen.

Typical examples of specific substituents on $R^{6a}$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Suitable examples of specific substituents on $R^{6a}$ include one, two or three substituents independently selected from fluoro.

Illustrative examples of specific values of $R^{6a}$ include methyl, ethyl, n-propyl, isopropyl, n-butyl, tert-butyl and difluorocyclobutyl.

Suitable examples of specific values of $R^{6a}$ include tert-butyl and difluorocyclobutyl.

Typically, $R^{6a}$ represents tert-butyl.

Typically, $R^{6b}$ represents hydrogen or methyl.

In a first embodiment, $R^{6b}$ represents hydrogen. In a second embodiment, $R^{6b}$ represents $C_{1-6}$ alkyl, especially methyl.

Typically, $R^{6c}$ represents hydrogen or methyl.

In a first embodiment, $R^{6c}$ represents hydrogen. In a second embodiment, $R^{6c}$ represents $C_{1-6}$ alkyl, especially methyl.

In a first embodiment, $R^7$ represents aryl, which group may be optionally substituted by one or more substituents. In a second embodiment, $R^7$ represents heteroaryl, which group may be optionally substituted by one or more substituents. In a third embodiment, $R^7$ represents spiro[($C_{3-7}$)heterocycloalkyl][heteroaryl], which group may be optionally substituted by one or more substituents.

Typical values of $R^7$ include phenyl, pyrazolo[1,5-a]pyrazinyl, benzoxazolyl, benzothiazolyl, benzimidazolyl, imidazo[1,2-b]pyridazinyl, imidazo[1,2-c]pyrimidinyl, purinyl, pyridinyl, pyridazinyl, cinnolinyl, pyrimidinyl, pyrazinyl and spiro[tetrahydropyranyl][indole], any of which groups may be optionally substituted by one or more substituents.

Typical examples of optional substituents on $R^7$ include one, two or three substituents independently selected from halogen, cyano, nitro, $C_{1-6}$ alkyl, difluoromethyl, trifluoromethyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Typical examples of particular substituents on $R^7$ include one, two or three substituents independently selected from fluoro, chloro, bromo, cyano, nitro, methyl, ethyl, isopropyl, tert-butyl, difluoromethyl, trifluoromethyl, phenyl, fluorophenyl, hydroxy, hydroxymethyl, oxo, methoxy, isopropoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Illustrative values of $R^7$ include phenyl, pyrazolo[1,5-a]pyrazinyl, benzoxazolyl, fluorobenzoxazolyl, methylbenzoxazolyl, benzothiazolyl, benzimidazolyl, fluoro-benzimidazolyl, imidazo[1,2-b]pyridazinyl, imidazo[1,2-c]pyrimidinyl, purinyl, pyridinyl, cyanopyridinyl, methylpyridinyl, methoxypyridinyl, pyridazinyl, chloropyridazinyl, cyanopyridazinyl, methylpyridazinyl, ethylpyridazinyl, isopropylpyridazinyl, difluoro-methylpyridazinyl, trifluoromethylpyridazinyl, methoxypyridazinyl, isopropoxy-pyridazinyl, difluoromethoxypyridazinyl, dimethylaminopyridazinyl, cinnolinyl, pyrimidinyl, pyrazinyl, methylpyrazinyl and spiro[tetrahydropyranyl][oxoindole].

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of particular substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

In general, $R^a$ represents $C_{1-6}$ alkyl, $C_{3-9}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted by one or more substituents.

Appositely, $R^a$ represents $C_{1-6}$ alkyl, $C_{3-9}$ cycloalkyl, aryl, $C_{3-7}$ heterocycloalkyl or heteroaryl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Illustrative values of $R^a$ include methyl, ethyl, cyclopropyl, phenyl, benzyl, oxetanyl, tetrahydropyranyl, piperidinyl, pyridinyl, pyridazinyl and isoindolylpropyl, any of which groups may be optionally substituted by one or more substituents.

Representative values of $R^a$ include methyl, cyclopentyl, phenyl, oxetanyl, tetrahydropyranyl, piperidinyl, pyridinyl and pyridazinyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy, oxo and $C_{1-6}$ alkylsulfonyl.

Selected examples of specific substituents on $R^a$ include methoxy, oxo and methylsulfonyl.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl.

In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl. In a further embodiment, $R^a$ represents optionally substituted $C_{3-9}$ cycloalkyl, e.g. cyclopentyl. In a further embodiment, $R^a$ represents optionally substituted $C_{3-7}$ heterocycloalkyl.

Particular values of $R^a$ include methyl, methoxyethyl, cyclopentyl, phenyl, benzyl, oxetanyl, tetrahydropyranyl, methylsulfonylpiperidinyl, dioxoisoindolylpropyl, pyridinyl and pyridazinyl.

In a particular aspect, $R^b$ represents hydrogen or trifluoromethyl; or $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

Favourably, $R^c$ represents $C_{3-7}$ heterocycloalkyl, which group may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected values of $R^c$ include tetrahydropyranyl and piperidinyl, either of which groups may be optionally substituted by one or more substituents.

Selected examples of suitable substituents on $R^c$ include $C_{1-6}$ alkylsulfonyl, $C_{2-6}$ alkylcarbonyl and $C_{2-6}$ alkoxycarbonyl.

Selected examples of specific substituents on $R^c$ include methylsulfonyl, acetyl and tert-butoxycarbonyl.

Specific values of $R^c$ include hydrogen, methyl, cyclobutyl, cyclopentyl, cyclohexyl, tetrahydropyranyl, methylsulfonylpiperidinyl, acetylpiperidinyl and tert-butoxycarbonylpiperidinyl.

Particular values of $R^c$ include tetrahydropyranyl and methylsulfonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin- 2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino ($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In another embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA) and N-oxides thereof, and pharmaceutically acceptable salts thereof:

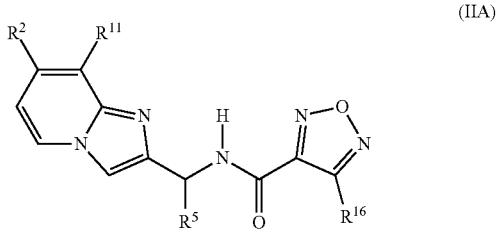

(IIA)

wherein $R^{11}$ represents hydrogen or halogen;

$R^{16}$ represents methyl or ethyl; and $R^2$ and $R^5$ are as defined above.

In a first embodiment, $R^{11}$ represents hydrogen. In a second embodiment, $R^{11}$ represents halogen, especially fluoro.

Suitably, $R^{11}$ represents hydrogen or fluoro.

In a first embodiment, $R^{16}$ represents methyl. In a second embodiment, $R^{16}$ represents ethyl.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments, including inflammatory and autoimmune disorders.

The compounds according to the present invention are useful in the treatment and/or prophylaxis of a pathological disorder that is mediated by a pro-inflammatory IL-17 cytokine or is associated with an increased level of a pro-inflammatory IL-17 cytokine. Generally, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, ankylosing spondylitis and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis, hypochlorhydia and pain (particularly pain associated with inflammation).

WO 2009/089036 reveals that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an Il-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis and microbial keratitis. Particular categories of Dry Eye Syndrome include keratoconjunctivitis sicca (KCS), Sjögren syndrome, Sjögren syndrome-associated keratoconjunctivitis sicca, non-Sjögren syndrome-associated keratoconjunctivitis sicca, keratitis sicca, sicca syndrome, xerophthalmia, tear film disorder, decreased tear production, aqueous tear deficiency (ATD), meibomian gland dysfunction and evaporative loss.

Illustratively, the compounds of the present invention may be useful in the treatment and/or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, inflammatory bowel diseases (including Crohn's disease and ulcerative colitis), ankylosing spondylitis and other spondyloarthropathies, cancer and pain (particularly pain associated with inflammation).

Suitably, the compounds of the present invention are useful in the treatment and/or prophylaxis of psoriasis, psoriatic arthritis or ankylosing spondylitis.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds according to the present invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds according to the present invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration the compounds according to the present invention may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound according to the present invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (IA) above may be prepared by a process which comprises reacting a carboxylic acid of formula $R^6$—$CO_2H$ with a compound of formula (III):

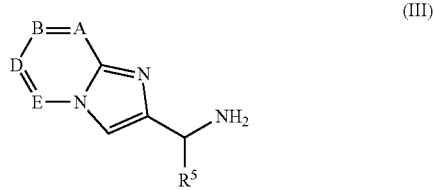

(III)

wherein A, B, D, E, $R^5$ and $R^6$ are as defined above.

The reaction is conveniently accomplished in the presence of a coupling agent and a base. Suitable coupling agents include 1-[bis(dimethylamino)methylene]-1H-1,2,3-triazolo[4,5-b]pyridinium 3-oxide hexafluorophosphate (HATU); 2,4,6-tripropyl-1,3,5,2,4,6-trioxatriphosphorinane-2,4,6-trioxide; and 2-chloro-1-methylpyridinium iodide. Suitable bases include organic amines, e.g. a trialkylamine such as N,N-diisopropylethylamine. The reaction is conveniently performed at ambient or elevated temperature in a suitable solvent, e.g. a cyclic ether such as tetrahydrofuran; or a dipolar aprotic solvent such as N,N-dimethylformamide or N,N-dimethylacetamide; or a chlorinated solvent such as dichloromethane.

Where $R^6$ represents $C_{1-6}$ alkyl, e.g. methyl, the compounds of formula (I) above may be prepared by a process which comprises reacting a compound of formula $R^6$—COCl, e.g. acetyl chloride, with a compound of formula (III) as defined above. The reaction is conveniently accomplished in the presence of a base. Suitable bases include organic amines, e.g. a trialkylamine such as N,N-diisopropylethylamine. The reaction is conveniently performed at ambient temperature in a suitable solvent, e.g. a cyclic ether such as tetrahydrofuran.

Where $R^6$ represents —$OR^{6a}$, the compounds of formula (I) above may be prepared by a two-step process which comprises: (i) reacting a compound of formula $R^{6a}$—OH with N,N'-disuccinimidyl carbonate, ideally in the presence of a base, e.g. an organic amine such as triethylamine; and (ii) reacting the resulting material with a compound of formula (III) as defined above. Steps (i) and (ii) are conveniently performed at ambient temperature in a suitable solvent, e.g. a chlorinated solvent such as dichloromethane.

The compounds of formula (IB) above may be prepared by a process which comprises reacting a compound of formula (III) as defined above with a compound of formula $L^1$-$S(O)_2R^6$, wherein $R^6$ is as defined above, and $L^1$ represents a suitable leaving group.

The leaving group $L^1$ is suitably a halogen atom, e.g. chloro.

The reaction is conveniently carried out at ambient temperature in the presence of pyridine. Alternatively, the reaction may be carried out at ambient temperature in the presence of a base, e.g. an organic amine such as N,N-diisopropylethylamine, in a suitable solvent, e.g. a chlorinated solvent such as dichloromethane.

The compounds of formula (IC) above may be prepared by a process which comprises reacting a compound of formula (III) as defined above with a compound of formula $L^2$-$R^7$, wherein $R^7$ is as defined above, and $L^2$ represents a suitable leaving group.

The leaving group $L^2$ is suitably a halogen atom, e.g. chloro or bromo.

The reaction is conveniently carried out in the presence of a base. Suitable bases include organic amines, e.g. a trialkylamine such as N,N-diisopropylethylamine. The reaction is typically performed at an elevated temperature in a suitable solvent, e.g. a cyclic ether such as 1,4-dioxane, or a cyclic amide such as 1-methyl-2-pyrrolidinone, or an organic sulfoxide such as dimethyl sulfoxide.

Alternatively, the reaction may be performed in the presence of a transition metal catalyst. Suitable transition metal catalysts of use in this procedure include [(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3). The reaction is conveniently carried out at an elevated temperature in the presence of a base, e.g. an inorganic base such as potassium tert-butoxide, in a suitable solvent or solvent mixture. The solvent or solvents may suitably be selected from a cyclic ether such as 1,4-dioxane, and a sulfoxide solvent such as dimethyl sulfoxide.

The intermediates of formula (III) above may be prepared by a procedure which comprises the following steps:

(i) reacting a compound of formula (IV) with a compound of formula (V):

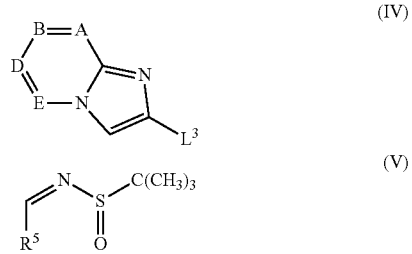

wherein A, B, D, E and $R^5$ are as defined above, and $L^3$ represents a suitable leaving group; to provide a compound of formula (VI):

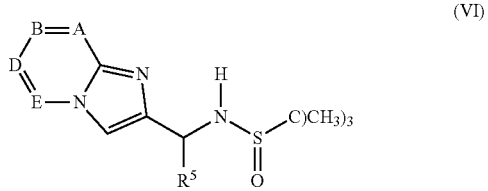

wherein A, B, D, E and $R^5$ are as defined above; and (ii) removal of the tert-butylsulfinyl group from compound (VI).

The leaving group $L^3$ will suitably be a halogen atom, e.g. bromo.

Step (i) is suitably effected by treatment of compound (IV) with a base, e.g. an organic base such as n-butyllithium, followed by reaction with compound (V). The reaction is conveniently accomplished in a suitable solvent, e.g. a chlorinated solvent such as dichloromethane; or a cyclic ether such as tetrahydrofuran.

Removal of the tert-butylsulfinyl group from compound (VI) in step (ii) may conveniently be accomplished by treatment with an acid, e.g. a mineral acid such as hydrochloric acid.

The intermediates of formula (V) above may be prepared by reacting an aldehyde derivative of formula $R^5$—CHO with 2-methyl-2-propanesulfinamide. The reaction is suitably effected in the presence of pyridinium p-toluenesulfonate and magnesium sulfate. The reaction is conveniently carried out at ambient temperature in a suitable solvent, e.g. a chlorinated solvent such as dichloromethane.

In an alternative procedure, the intermediates of formula (III) above may be prepared by removal of the N-protecting group $R^p$ from a compound of formula (VII):

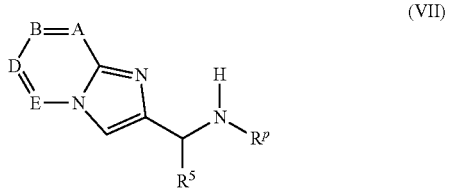

wherein A, B, D, E and $R^5$ are as defined above, and $R^p$ represents a N-protecting group.

The N-protecting group $R^p$ will suitably be tert-butoxycarbonyl (BOC), in which case the removal thereof may conveniently be effected by treatment with an acid, e.g. a mineral acid such as hydrochloric acid, or an organic acid such as trifluoroacetic acid.

Alternatively, the N-protecting group $R^p$ may be benzyloxycarbonyl, in which case the removal thereof may conveniently be effected by catalytic hydrogenation, typically by treatment with hydrogen gas or ammonium formate in the presence of a hydrogenation catalyst, e.g. palladium on charcoal, or palladium hydroxide on charcoal.

The intermediates of formula (VII) above may be prepared by reacting a compound of formula (VIII) with a compound of formula (IX):

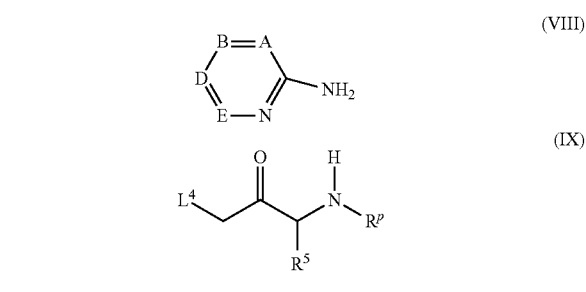

wherein A, B, D, E, $R^5$ and $R^p$ are as defined above, and $L^4$ represents a suitable leaving group.

The leaving group $L^4$ is typically a halogen atom, e.g. bromo.

The reaction is conveniently effected at an elevated temperature in a suitable solvent, e.g. a $C_{1-4}$ alkanol such as isopropanol.

The compounds of formula (ID) above may be prepared by a process which comprises reacting a compound of formula $R^7$—NH2 with a compound of formula (X):

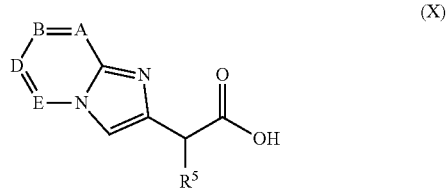

wherein A, B, D, E, $R^5$ and $R^7$ are as defined above; under conditions analogous to those described above for the reaction between compound (III) and a carboxylic acid of formula $R^6$—$CO_2H$.

Where they are not commercially available, the starting materials of formula (IV), (VIII), (IX) and (X) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N—BOC moiety (wherein BOC is an abbreviation for tert-butoxycarbonyl) may be converted into the corresponding compound comprising a N—H moiety by treatment with an acid, e.g. a mineral acid such as hydrochloric acid, or an organic acid such as trifluoroacetic acid.

A compound of formula (I) comprising a N—H functionality may be alkylated, e.g. methylated, by treatment with a suitable alkyl halide, e.g. iodomethane, typically in the presence of a base, e.g. an inorganic carbonate such as sodium carbonate.

A compound of formula (I) comprising a N—H functionality may be acylated, e.g. acetylated, by treatment with a suitable acyl halide, e.g. acetyl chloride, typically in the presence of a base, e.g. an organic base such as N,N-diisopropylethylamine or triethylamine. Similarly, a compound of formula (I) comprising a N—H functionality may be acylated, e.g. acetylated, by treatment with a suitable acyl anhydride, e.g. acetic anhydride, typically in the presence of a base, e.g. an organic base such as triethylamine.

Similarly, a compound of formula (I) comprising a N—H functionality may be converted into the corresponding compound comprising a N—S(O)$_2$Alk$^1$ functionality (wherein Alk$^1$ represents C$_{1-4}$ alkyl, e.g. methyl) by treatment with the appropriate C$_{1-4}$ alkylsulfonyl chloride reagent, e.g. methylsulfonyl chloride, typically in the presence of a base, e.g. an organic base such as triethylamine.

Similarly, a compound of formula (I) comprising a N—H functionality may be converted into the corresponding compound comprising a carbamate or urea moiety respectively by treatment with the appropriate chloroformate or carbamoyl chloride reagent, typically in the presence of a base, e.g. an organic base such as triethylamine. Alternatively, a compound of formula (I) comprising a N—H functionality may be converted into the corresponding compound comprising a urea moiety by treatment with the appropriate amine-substituted (3-methylimidazol-3-ium-1-yl)methanone iodide derivative, typically in the presence of a base, e.g. an organic base such as triethylamine. Alternatively, a compound of formula (I) comprising a N—H functionality may be converted into the corresponding compound comprising a urea moiety N—C(O)N(H)Alk$^1$ (wherein Alk$^1$ is as defined above) by treatment with the appropriate isocyanate derivative Alk$^1$-N=C=O, typically in the presence of a base, e.g. an organic base such as triethylamine.

A compound of formula (I) comprising a N—H functionality may be converted into the corresponding compound comprising a N—C(H) functionality by treatment with the appropriate aldehyde or ketone in the presence of a reducing agent such as sodium triacetoxyborohydride.

A compound may be alkylated by treatment with a suitably substituted alkyl trifluoromethanesulfonate, typically in the presence of a base, e.g. a dialkylamide salt such as lithium diisopropylamide.

A compound of formula (I) comprising a C$_{1-4}$ alkoxycarbonyl moiety —CO$_2$Alk$^1$ (wherein Alk$^1$ is as defined above) may be converted into the corresponding compound comprising a carboxylic acid (—CO$_2$H) moiety by treatment with a base, e.g. an alkali metal hydroxide salt such as lithium hydroxide. Alternatively, a compound of formula (I) comprising a tert-butoxycarbonyl moiety may be converted into the corresponding compound comprising a carboxylic acid (—CO$_2$H) moiety by treatment with trifluoroacetic acid.

A compound of formula (I) comprising a carboxylic acid (—CO$_2$H) moiety may be converted into the corresponding compound comprising an amide moiety by treatment with the appropriate amine, under conditions analogous to those described above for the reaction between compound (III) and a carboxylic acid of formula R$^6$—CO$_2$H.

A compound of formula (I) comprising a C$_{1-4}$ alkoxycarbonyl moiety —CO$_2$Alk$^1$ (wherein Alk$^1$ is as defined above) may be converted into the corresponding compound comprising a hydroxymethyl (—CH$_2$OH) moiety by treatment with a reducing agent such as lithium aluminium hydride.

A compound of formula (I) comprising a C$_{1-4}$ alkylcarbonyloxy moiety —OC(O)Alk$^1$ (wherein Alk$^1$ is as defined above), e.g. acetoxy, may be converted into the corresponding compound comprising a hydroxy (—OH) moiety by treatment with a base, e.g. an alkali metal hydroxide salt such as sodium hydroxide.

A compound of formula (I) comprising a halogen atom, e.g. bromo, may be converted into the corresponding compound comprising an optionally substituted aryl, heterocycloalkenyl or heteroaryl moiety by treatment with the appropriately substituted aryl, heterocycloalkenyl or heteroaryl boronic acid or a cyclic ester thereof formed with an organic diol, e.g. pinacol, 1,3-propanediol or neopentyl glycol. The reaction is typically effected in the presence of a transition metal catalyst, and a base. The transition metal catalyst may be [1,1'-bis(diphenylphosphino)ferrocene]dichloropalladium(II). In the alternative, the transition metal catalyst may be tris(dibenzylideneacetone)dipalladium(0), which may advantageously be employed in conjunction with 2-dicyclohexylphosphino-2',4',6'-triisopropylbiphenyl (XPhos). Suitably, the base may be an inorganic base such as sodium carbonate or potassium carbonate.

A compound of formula (I) comprising a halogen atom, e.g. chloro or bromo, may be converted into the corresponding compound comprising an optionally substituted aryl, heterocycloalkenyl or heteroaryl moiety via a two-step procedure which comprises: (i) reaction with bis(pinacolato)diboron; and (ii) reaction of the compound thereby obtained with an appropriate bromoaryl, heterocycloalkenyl or bromoheteroaryl derivative substituted with a suitable leaving group, e.g. a halogen atom such as bromo, or a sulfonyloxy moiety such as trifluoromethylsulfonyloxy. Step (i) is conveniently effected in the presence of a transition metal catalyst, and a base such as potassium acetate. Suitably, the transition metal catalyst may be tris(dibenzylideneacetone)dipalladium(0), which may advantageously be employed in conjunction with 2-dicyclohexylphosphino-2',4',6'-triisopropylbiphenyl (XPhos). Alternatively, the transition metal catalyst may be [1,1'-bis(diphenylphosphino)ferrocene]dichloropalladium(II). Step (ii) is conveniently effected in the presence of a transition metal catalyst such as [1,1'-bis(diphenylphosphino)-ferrocene]dichloropalladium(II), and a base, e.g. an inorganic base such as sodium carbonate or potassium carbonate.

A compound comprising a halogen atom, e.g. bromo, may be converted into the corresponding compound comprising a tert-butoxycarbonylmethyl moiety by treatment with tert-butyl 2-(bromozincio)acetate. The reaction is conveniently carried out in the presence of a transition metal catalyst, e.g. allylpalladium(II) chloride, which will generally be employed in conjunction with XPhos.

A compound of formula (I) comprising a cyano (—CN) moiety may be converted into the corresponding compound comprising a 1-aminoethyl moiety by a two-step process which comprises: (i) reaction with methylmagnesium chloride, ideally in the presence of titanium(IV) isopropoxide; and (ii) treatment of the resulting material with a reducing agent such as sodium borohydride. If an excess of methylmagnesium chloride is employed in step (i), the corresponding compound comprising a 1-amino-1-methylethyl moiety may be obtained.

A compound of formula (I) comprising the moiety —S— may be converted into the corresponding compound comprising the moiety —S(O)(NH)— by treatment with (diacetoxyiodo)benzene and ammonium carbamate.

A compound of formula (I) comprising a C=C double bond may be converted into the corresponding compound comprising a CH—CH single bond by treatment with gaseous hydrogen in the presence of a hydrogenation catalyst, e.g. palladium on charcoal.

A compound of formula (I) comprising an aromatic nitrogen atom may be converted into the corresponding compound comprising an N-oxide moiety by treatment with a suitable oxidising agent, e.g. 3-chloroperbenzoic acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Greene's Protective Groups in Organic Synthesis*, ed. P. G. M. Wuts, John Wiley & Sons, 5$^{th}$ edition, 2014. The protecting groups may be removed at any convenient subsequent stage utilising methods known from the art.

The compounds in accordance with this invention potently inhibit the ability of IL-17A to bind to IL-17RA. When tested in the IL-17 FRET assay described below, compounds of the present invention exhibit an IC$_{50}$ value of 10 µM or less, generally of 5 µM or less, usually of 1 µM or less, typically of 500 nM or less, suitably of 100 nM or less, ideally of 50 nM or less, and preferably of 25 nM or less (the skilled person will appreciate that a lower IC$_{50}$ figure denotes a more active compound).

Moreover, certain compounds in accordance with this invention potently inhibit IL-17 induced IL-6 release from human dermal fibroblasts. Indeed, when tested in the HDF cell line assay described below, compounds of the present invention exhibit an IC$_{50}$ value of 10 µM or less, generally of 5 µM or less, usually of 1 µM or less, typically of 500 nM or less, suitably of 100 nM or less, ideally of 50 nM or less, and preferably of 25 nM or less (as before, the skilled person will appreciate that a lower IC$_{50}$ figure denotes a more active compound).

IL-17 FRET Assay

The purpose of this assay is to test the ability of compounds to disrupt the interaction between IL-17A and soluble IL-17 Receptor A (IL-17RA). The ability of a compound to inhibit IL-17A binding to IL-17RA is measured in this assay.

An IL-17AA-TEV-Human Fc construct was expressed in a CHO SXE cell system and purified by protein A chromatography and size exclusion. The protein was labelled with an amine reactive AlexaFluor 647 dye (Thermo Fisher #A20006), as per manufacturer's instruction.

Soluble IL-17RA (33-317)-HKH-TEV-Fc was expressed in an Expi HEK293 cell system and purified by protein A chromatography and size exclusion. The Fc tag was cleaved by TEV, producing IL-17RA (33-317)-HKH, and the protein was labelled with amine reactive terbium (Thermo Fisher #PV3581).

In assay buffer [Dulbecco's PBS (Sigma #14190-094), 0.05% P20 (Thermo Scientific #28320), 1 mg/mL BSA (Sigma #A2153-500G)] the following solutions were prepared:

For IL-17A assay

IL-17A-Fc-AF647 at 5 nM

IL-17RA-HKH-Tb at 5 nM

Compounds were serially diluted in DMSO before receiving an aqueous dilution into a 384 well dilution plate (Greiner #781281), to give a 25% DMSO solution.

IL-17A (10 µL) was added to a black low volume assay plate (Costar #4511) and diluted compound (5 µL) was transferred from the aqueous dilution plate. The cytokine and compound were allowed to incubate for 1 h, then IL-17RA (10 µL) was added. The plates were wrapped in foil and incubated at room temperature for 18-20 h with gentle shaking (<400 rpm) before being read on a Perkin Elmer Envision plate reader (Excitation: 330 nm; Emission 615/645 nm).

The final assay concentrations were IL-17A-AF647 2 nM and IL-17RA-Tb 2 nM, 5% DMSO.

When tested in the IL-17 FRET assay, the compounds of the accompanying Examples were all found to exhibit IC$_{50}$ values of 10 µM or better.

When tested in the IL-17 FRET assay, compounds of the accompanying Examples exhibit IC$_{50}$ values generally in the range of about 0.01 nM to about 10 µM, usually in the range of about 0.01 nM to about 5 µM, typically in the range of about 0.01 nM to about 1 µM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

Inhibition of IL-17A Induced IL-6 Release from Dermal Fibroblast Cell Line

The purpose of this assay is to test the neutralising ability to IL-17 proteins, in a human primary cell system. Stimulation of normal human dermal fibroblasts (HDF) with IL-17 alone produces only a very weak signal but in combination with certain other cytokines, such as TNFα, a synergistic effect can be seen in the production of inflammatory cytokines, i.e. IL-6.

HDFs were stimulated with IL-17A (50 pM) in combination with TNF-α (25 pM). The resultant IL-6 response was then measured using a homogenous time-resolved FRET kit from Cisbio. The kit utilises two monoclonal antibodies, one labelled with Eu-Cryptate (Donor) and the second with d2 or XL665 (Acceptor). The intensity of the signal is proportional to the concentration of IL-6 present in the sample (Ratio is calculated by 665/620×104).

The ability of a compound to inhibit IL-17 induced IL-6 release from human dermal fibroblasts is measured in this assay.

HDF cells (Sigma #106-05n) were cultured in complete media (DMEM+10% FCS+2 mM L-glutamine) and maintained in a tissue culture flask using standard techniques. Cells were harvested from the tissue culture flask on the morning of the assay using TrypLE (Invitrogen #12605036). The TrypLE was neutralised using complete medium (45 mL) and the cells were centrifuged at 300×g for 3 minutes. The cells were re-suspended in complete media (5 mL) counted and adjusted to a concentration of $3.125 \times 10^4$ cells/mL before being added to the 384 well assay plate (Corning #3701) at 40 μL per well. The cells were left for a minimum of three hours, at 37° C./5% $CO_2$, to adhere to the plate.

Compounds were serially diluted in DMSO before receiving an aqueous dilution into a 384 well dilution plate (Greiner #781281), where 5 μL from the titration plate was transferred to 45 μL of complete media and mixed to give a solution containing 10% DMSO.

Mixtures of TNFα and IL-17 cytokine were prepared in complete media to final concentrations of TNFα 25 pM/IL-17A 50 pM, then 30 μL of the solution was added to a 384 well reagent plate (Greiner #781281).

10 μL from the aqueous dilution plate was transferred to the reagent plate containing 30 μL of the diluted cytokines, to give a 2.5% DMSO solution. The compounds were incubated with the cytokine mixtures for one hour at 37° C. After the incubation, 10 μL was transferred to the assay plate, to give a 0.5% DMSO solution, then incubated for 18-20 h at 37° C./5% $CO_2$.

From the Cisbio IL-6 FRET kit (Cisbio #62IL6PEB) europium cryptate and Alexa 665 were diluted in reconstitution buffer and mixed 1:1, as per kit insert. To a white low volume 384 well plate (Greiner #784075) were added FRET reagents (10 μL), then supernatant (10 μL) was transferred from the assay plate to Greiner reagent plate. The mixture was incubated at room temperature for 3 h with gentle shaking (<400 rpm) before being read on a Synergy Neo 2 plate reader (Excitation: 330 nm; Emission: 615/645 nm).

When tested in the above assay, compounds of the accompanying Examples were found to exhibit $IC_{50}$ values of 10 μM or better.

When tested in the above assay, compounds of the accompanying Examples exhibit $IC_{50}$ values generally in the range of about 0.01 nM to about 10 μM, usually in the range of about 0.01 nM to about 5 μM, typically in the range of about 0.01 nM to about 1 μM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

The following Examples illustrate the preparation of compounds according to the invention.

EXAMPLES

Abbreviations

DCM: dichloromethane EtOAc: ethyl acetate
MeOH: methanol THF: tetrahydrofuran
DMSO: dimethyl sulfoxide DIPEA: N,N-diisopropylethylamine
TBME: tert-butyl methyl ether IPA: isopropyl alcohol
DMA: N,N-dimethylacetamide
HATU: 1-[bis(dimethylamino)methylene]-1H-1,2,3-triazolo[4,5-b]pyridinium 3-oxid hexafluorophosphate
$Pd_2(dba)_3$: tris(dibenzylideneacetone)dipalladium(0)
$Pd(dppf)Cl_2$: [1,1'-bis(diphenylphosphino)ferrocene]dichloropalladium(II)
XPhos: 2-dicyclohexylphosphino-2',4',6'-triisopropylbiphenyl
h: hour r.t.: room temperature
M: mass RT: retention time
FCC: flash column chromatography
HPLC: High Performance Liquid Chromatography
LCMS: Liquid Chromatography Mass Spectrometry
Analytical Conditions Compounds were named with the aid of ACD/Name Batch (Network) version 11.01, and/or Accelrys Draw 4.2, and/or Elemental, Dotmatics, and/or Chemaxon.

All reactions involving air- or moisture-sensitive reagents were performed under a nitrogen atmosphere using dried solvents and glassware.

NMR spectra were recorded on a Bruker Avance III HD 500 MHz, 400 MHz, 300 MHz or 250 MHz spectrometer.

Column chromatography separations were performed using a Biotage® Isolera 4 system with Biotage® SNAP KP-Sil pre-packed silica gel columns.

HPLC-MS was performed on an Agilent 1200-6120 LC-MS system coupled to UV Detection (230 to 400 nm and 215 nm) and Mass Spec Detection Agilent 6120 Mass Spectrometer (ES) m/z 120 to 800.

Method 1

Stationary Phase: X-Bridge C18 Waters 2.1×20 mm, 2.5 μm column
Mobile Phase A: 10 nM ammonium formate in water+0.1% $NH_3$ (pH 10)
Mobile Phase B: acetonitrile+5% water+0.1% $NH_3$ (pH 10)
Flow rate: 1 mL/minute
Gradient Program:

| Time | A % | B % |
| --- | --- | --- |
| 0.00 | 95.00 | 5.00 |
| 1.50 | 5.00 | 95.00 |
| 2.25 | 5.00 | 95.00 |
| 2.50 | 95.00 | 5.00 |

Method 2
Acquity UPLC BEH C18 1.7 μm, 2.1×50 mm column
Mobile Phase A: 10 mM ammonium formate+0.1% $NH_3$ (pH 10)
Mobile Phase B: acetonitrile+5% $H_2O$+0.1% $NH_3$ (pH 10)
Flow rate: 1.5 mL/minute Gradient program:

| Time | A % | B % |
|---|---|---|
| 0.00 | 95.00 | 5.00 |
| 0.10 | 95.00 | 5.00 |
| 3.50 | 5.00 | 95.00 |
| 4.00 | 5.00 | 95.00 |
| 4.05 | 95.00 | 5.00 |

Method 3

XBridge Prep C18 (19×100 mm, 5 μm) column
Mobile Phase A: 10 mM ammonium bicarbonate in water+0.1% NH₃ (pH 10)
Mobile Phase B: acetonitrile+5% water+0.1% NH₃ (pH 10)
Flow rate: 19 mUJminute
Gradient program:

| Time | A % | B % |
|---|---|---|
| 0.00 | 65.00 | 35.00 |
| 2.50 | 65.00 | 35.00 |
| 11.00 | 50.00 | 50.00 |
| 11.50 | 5.00 | 95.00 |
| 13.00 | 65.00 | 35.00 |

Method 4

Stationary Phase: X-Bridge C18 Waters 2.1×20 mm, 2.5 μm column
Mobile Phase A: 10 nM ammonium formate in water+0.1% ammonia solution
Mobile Phase B: acetonitrile+5% water+0.1% ammonia solution
Flow rate: 1 mL/minute
Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 5 uPLC-MS was performed on a Waters Acquity UPLC system coupled to a Waters Acquity PDA detector, an ELS detector and an MSD (Scan Positive: 150-850).
Stationary phase: Phenomenex Kinetex-XB, C18 2.1×100 mm, 1.7 μm column
Mobile Phase A: 0.1% formic acid in water
Mobile Phase B: 0.1% formic acid in acetonitrile
Flow rate: 0.6 mL/minute
Gradient program:

| Time | A % | B % |
|---|---|---|
| 0.00 | 95.00 | 5.00 |
| 5.30 | 0.00 | 100.0 |
| 5.80 | 0.00 | 100.0 |
| 5.82 | 95.00 | 5.00 |
| 7.00 | 95.00 | 5.00 |

Intermediate 1

(NE)-2-Methyl-N-[(4-trans-methylcyclohexyl)methylene]propane-2-sulfinamide trans-4-Methylcyclohexanecarbaldehyde (8.7 g, 69 mmol), 2-methylpropane-2-sulfinamide (9.2 g, 76 mmol), pyridinium p-toluenesulfonate (870 mg, 3.4 mmol) and magnesium sulfate (41 g, 340 mmol) were suspended in DCM (140 mL). The mixture was stirred at ambient temperature for 18 h, then filtered and concentrated in vacuo. The resulting material was purified by flash column chromatography, using a gradient of EtOAc in isohexanes (0-20/6), to afford the title compound (4.1 g, 26%) as a pale yellow oil. $\delta_H$ (400 MHz, CDCl₃) 7.96 (d, J 4.8 Hz, 1H), 2.37 (tdt, J 12.0, 4.8, 3.6 Hz, 1H), 1.98-1.84 (m, 2H), 1.85-1.72 (m, 2H), 1.41-1.23 (m, 3H), 1.18 (s, 9H), 1.09-0.93 (m, 2H), 0.91 (d, J 6.5 Hz, 3H). HPLC-MS (ES+) (Method 1): MH+ m/z 230, RT 1.43 minutes.

Intermediate 2

(7-Chloroimidazo[1,2-a]pyridin-2-yl)(4-trans-methylcyclohexyl)methanamine hydrochloride 2-Bromo-7-chloroimidazo[1,2-a]pyridine (500 mg, 2.2 mmol) was dissolved in DCM (20 mL) and cooled to −78° C., then a solution of n-butyllithium (1.6M in hexanes, 1.6 mL, 2.5 mmol) was added. The mixture was stirred at −78° C., then a solution of Intermediate 1 (495 mg, 2.2 mmol) in DCM (20 mL) was added over 5 minutes. The solution was stirred at −78° C. for 1 h, then allowed to warm to ambient temperature and stirred for 4 h. A 4N solution of HCl in 1,4-dioxane (10 mL) was added. The mixture was stirred at ambient temperature for 30 minutes, then concentrated in vacuo to afford the title compound (600 mg), which was utilised without further purification. HPLC-MS (ES+) (Method 1): MH+ m/z 278, 280, RT 1.17 minutes.

Intermediate 3

N-[(7-Chloroimidazo[1,2-a]pyridin-2-yl)(4-trans-methylcyclohexyl)methyl]-4-methyl-1,2,5-oxadiazole-3-carboxamide Intermediate 2 (600 mg, 2.16 mmol) was dissolved in DCM (20 mL), then 4-methyl-1,2,5-oxadiazole-3-carboxylic acid (277 mg, 2.16 mmol), DIPEA (1.51 mL, 8.64 mmol) and HATU (1 g, 2.59 mmol) were added. The mixture was stirred at ambient temperature for 18 h, then diluted with DCM (50 mL) and washed with water (50 mL). The aqueous layer was further extracted with DCM (50 mL), then the combined organic layers were washed with brine (50 mL), dried over Na₂SO₄ and concentrated in vacuo. The crude material was purified by flash column chromatography, eluting with a gradient of MeOH/DCM (0-10/6), to afford the title compound (636 mg, 76%). $\delta_H$ (400 MHz, CDCl₃) 7.99 (dd, J 7.2, 0.8 Hz, 1H), 7.75-7.61 (m, 1H), 7.60-7.53 (m, 1H), 7.47 (s, 1H), 6.78 (dd, J 7.2, 2.1 Hz, 1H), 5.08 (dd, J 9.0, 7.8 Hz, 1H), 3.70 (s, 3H), 3.18 (qd, J 7.4, 3.9 Hz, 1H), 2.59 (s, 3H), 1.49-1.39 (m, 9H). HPLC-MS (ES+) (Method 1): MH+ m/z 388, 390, RT 1.45 minutes.

Intermediate 4

O¹-tert-Butyl O³-ethyl 4-(trifluoromethylsulfonyloxy)-2,5-dihydropyrrole-1,3-dicarboxylate 1-tert-Butyl 3-ethyl 4-oxopyrrolidine-1,3-dicarboxylate (15.0 g, 55.4 mmol) was dissolved in DCM (80 mL) and cooled under nitrogen to −78° C. in a dry ice/acetone bath. DIPEA (10.6 mL, 61.0 mmol) was added. The reaction mixture was stirred under nitrogen, then a 1M solution of trifluoromethanesulfonic anhydride in DCM (58 mL, 58 mmol) was added. The reaction mixture was stirred at −78° C. under nitrogen for 30 minutes, then warmed to room temperature and stirred for 18 h. Saturated aqueous sodium hydrogen carbonate solution (50 mL) was added. The mixture was stirred at r.t. for 5 minutes, then filtered through a hydrophobic PTFE frit, washing with DCM (25 mL). The combined filtrates were concentrated in vacuo. The resulting oil was dissolved in diethyl ether (150 mL) and the resultant white solids were filtered off, washing with diethyl ether (2×25 mL). The filtrates were concentrated in vacuo. The crude material was purified by flash column chromatography, using a gradient of EtOAc in isohexanes (0-20/6), to afford the title compound (14.3 g, 66%) as a colourless oil which solidified upon standing. $\delta_H$ (400 MHz, CDCl$_3$) 4.47-4.28 (m, 4H), 4.23 (q, J 7.1 Hz, 2H), 1.42 (d, J 1.4 Hz, 9H), 1.24 (t, J 7.1 Hz, 3H).

Intermediate 5

O$^1$-tert-Butyl O$^3$-ethyl 4-(2-{(4-trans-methylcyclohexyl)[(4-methyl-1,2,5-oxadiazole-3-carbonyl)amino]methyl}imidazo[1,2-a]pyridin-7-yl)-2,5-dihydropyrrole-1,3-dicarboxylate Intermediate 3 (280 mg, 0.722 mmol), bis(pinacolato) diboron (220 mL, 0.866 mmol), potassium acetate (143 mg, 1.44 mmol) and XPhos (35 mg, 0.0722 mmol) were suspended in 1,4-dioxane (5 mL) and sealed in a vial which was degassed with three cycles of vacuum and nitrogen. Pd$_2$(dba)$_3$ (34 mg, 0.0361 mmol) was added. The reaction mixture was heated at 100° C. for 7 h, then cooled, filtered through celite and concentrated in vacuo. The crude material was dissolved in a mixture of 1,4-dioxane (5 mL) and water (5 mL), then Intermediate 4 (422 mg, 1.08 mmol) and potassium carbonate (302 mg, 2.17 mmol) were added. The mixture was sealed in a vial which was degassed with three cycles of vacuum and nitrogen. Pd(dppf)Cl$_2$ (28 mg, 0.0361 mmol) was added. The mixture heated at 100° C. for 2 h, then cooled to ambient temperature and diluted with DCM (20 mL). The organic phase was separated using a hydrophobic PTFE frit, then concentrated in vacuo. The crude material was purified by flash column chromatography, eluting with MeOH in DCM (0-10%), to afford the title compound (291 mg, 68%), which was utilised without further purification. HPLC-MS (ES+) (Method 1): MH+ m/z 593, RT 1.62 minutes.

Intermediate 6

1-tert-Butoxycarbonyl-4-(2-{(4-trans-methylcyclohexyl)[(4-methyl-1,2,5-oxadiazole-3-carbonyl)amino]methyl}imidazo[1,2-a]pyridin-7-yl)-2,5-dihydropyrrole-3-carboxylic acid Intermediate 5 (291 mg, 0.491 mmol) was dissolved in a mixture of THF (5 mL) and water (5 mL), then lithium hydroxide (24 mg, 0.982 mmol) was added. The mixture was stirred at ambient temperature for 3 h, then 2N hydrochloric acid (2 mL) was added. The mixture was extracted into DCM (2×25 mL). The combined organic layers were dried over Na$_2$SO$_4$ and concentrated in vacuo to afford the title compound (347 mg, 100%), which was utilised without further purification. HPLC-MS (ES+) (Method 1): MH+ m/z 565, RT 1.16 minutes.

Intermediate 7

Benzyl N-{(1S)-1-(4,4-difluorocyclohexyl)-2-[methoxy(methyl)amino]-2-oxoethyl}-carbamate To a stirred solution of (2S)-2-(benzyloxycarbonylamino)-2-(4,4-difluoro-cyclohexyl)acetic acid (9.00 g, 27.5 mmol) and N-methoxymethanamine hydrochloride (3.22 g, 33.0 mmol) in DCM (90 mL) was added HATU (12.55 g, 33.0 mmol) portion-wise, followed by DIPEA (12 mL, 68.7 mmol) dropwise, at ambient temperature. The reaction mixture was stirred at ambient temperature for 45 minutes. Saturated aqueous sodium carbonate solution (50 mL) and water (50 mL) were added to the reaction mixture, and stirring was continued for 5 minutes. The organic phase was collected, and the aqueous phase was back-extracted with DCM (100 mL). The organic layers were combined and washed with brine (100 mL), then dried over anhydrous sodium sulfate and filtered. The solvent was removed in vacuo. The residue was purified by automated chromatography (350 g SFAR-duo column), eluting with a gradient of TBME in heptane (5-70%), to afford the title compound (10.01 g, 92%) as a clear gum. $\delta_H$ (400 MHz, CDCl$_3$) 7.40-7.28 (m, 5H), 5.42 (d, J 9.4 Hz, 1H), 5.12 (d, J 12.3 Hz, 1H), 5.07 (d, J 12.2 Hz, 1H), 4.80-4.65 (m, 1H), 3.78 (s, 3H), 3.22 (s, 3H), 2.16-2.04 (m, 2H), 1.86-1.63 (m, 5H), 1.56-1.37 (m, 2H). $^{19}$F NMR (376 MHz, CDCl$_3$) δ −92.13 (d, J 236 Hz), −102.20 (d, J 236 Hz). HPLC-MS (Method 1): MH+ m/z 371, RT 2.85 minutes.

Intermediate 8

Benzyl N-[(1S)-1-(4,4-difluorocyclohexyl-2-oxopropyl]carbamate

To a stirred solution of Intermediate 7 (10.0 g, 25.4 mmol) in anhydrous THF (132 mL), previously cooled to −20° C., was added 3M methylmagnesium bromide in diethyl ether (25 mL, 76.1 mmol) dropwise, maintaining the temperature below −10° C.

The reaction mixture was stirred for 4.5 h, and the temperature was gently raised to ambient temperature. The reaction mixture was cooled to 0° C. and added dropwise to ice-cold saturated aqueous ammonium chloride solution (300 mL). Stirring was continued at 0° C. for a further 5 minutes, then the reaction mixture was extracted with ethyl acetate (2×200 mL). The organic layers were combined and washed with brine (140 mL), then dried over anhydrous sodium sulfate and filtered. The solvent was removed in vacuo to afford the title compound (7.98 g, 95%) as an off-white solid. $\delta_H$ (500 MHz, CDCl$_3$) 7.40-7.30 (m, 5H), 5.43 (d, J 8.2 Hz, 1H), 5.12 (d, J 12.2 Hz, 1H), 5.08 (d, J 12.2 Hz, 1H), 4.45 (dd, J 8.5, 4.1 Hz, 1H), 2.24 (s, 3H), 2.18-2.07 (m, 2H), 1.98-1.88 (m, 1H), 1.87-1.79 (m, 1H), 1.79-1.59 (m, 2H), 1.56-1.42 (m, 2H), 1.38 (td, J 13.0, 3.5 Hz, 1H). $^{19}$F NMR (471 MHz, CDCl$_3$) δ −91.82 (d, J 237 Hz), −102.71 (d, J 237 Hz). HPLC-MS (Method 1): MH+ m/z 326, RT 2.83 minutes.

Intermediate 9

Benzyl N-[(1S)-3-bromo-1-(4,4-difluorocyclohexyl-2-oxopropyl]carbamate

To a stirred solution of Intermediate 8 (1.18 g, 3.63 mmol) in chloroform (12 mL), cooled to 0° C., was added bromine (0.2 mL, 3.63 mmol) dropwise over 5 minutes. The reaction mixture was stirred at ambient temperature for 3 h, then the solvent was removed in vacuo. The residue was partitioned between water (5 mL) and ethyl acetate (10 mL). The organic layer was further washed with saturated aqueous sodium carbonate solution (5 mL) and brine (5 mL), then dried over anhydrous sodium sulfate and filtered. The solvent was removed in vacuo. The residue was purified using automated chromatography (Isolera 4, 50 g SFAR Duo column), eluting with a gradient of TBME in heptane (5-50/6), to afford the title compound (0.35 g, 24%) as an off-white solid. $\delta_H$ (400 MHz, CDCl$_3$) 7.43-7.28 (m, 5H), 5.35 (d, J 8.5 Hz, 1H), 5.11 (s, 2H), 4.66 (dd, J 8.4, 5.2 Hz, 1H), 4.05 (d, J 13.2 Hz, 1H), 4.00 (d, J 13.2 Hz, 1H), 2.22-2.05 (m, 2H), 2.03-1.89 (m, 1H), 1.85-1.45 (m, 5H), 1.44-1.31 (m, 1H). $^{19}$F NMR (376 MHz, CDCl$_3$) δ −92.09 (d, J 237 Hz), −102.59 (d, J 237 Hz). HPLC-MS (Method 1): MH+ m/z 404/406 (Br pattern), RT 3.10 minutes.

Intermediate 10

Benzyl N—[(S)-(7-bromo-8-fluoroimidazo[1,2-a] pyridin-2-yl)(4,4-difluorocyclohexyl)-methyl]carbamate A suspension of 4-bromo-3-fluoropyridin-2-amine (520 mg, 2.72 mmol) and Intermediate 9 (912 mg, 2.26 mmol) in IPA (9 mL) was sealed under nitrogen and heated at 80° C. for 24 h. After cooling, the mixture was diluted with water (30 mL) and extracted with ethyl acetate (3×30 mL). The combined organic extracts were washed with brine (30 mL), dried over magnesium sulfate and concentrated in vacuo. The resulting crude brown viscous oil (1.54 g) was purified by FCC (100 g Biotage Isolera Sfar Duo column), eluting with 0-50% EtOAc in heptane, to afford the title compound (632 mg, 57%) as a tan powder. $\delta_H$ (400 MHz, 356 K, DMSO-d6) 8.33 (dd, J 7.2, 0.7 Hz, 1H), 7.93 (d, J 3.1 Hz, 1H), 7.44 (br s, 1H), 7.39-7.21 (m, 5H), 7.05 (dd, J 7.2, 6.0 Hz, 1H), 5.07 (d, J 12.7 Hz, 1H), 5.03 (d, J 12.7 Hz, 1H), 4.73 (dd, J 9.1, 7.4 Hz, 1H), 2.13-1.89 (m, 3H), 1.86-1.56 (m, 4H), 1.48-1.19 (m, 2H). $^{19}$F NMR (376 MHz, 356 K, DMSO-d6) δ −90.04 (d, J 233 Hz), −99.39 (d, J 233 Hz), −125.77. HPLC-MS (Method 1): MH+ m/z 496/498 (Br pattern), RT 1.96 minutes.

Intermediate 11 tert-Butyl 2-{2-[(S)-benzyloxycarbonylamino(4,4-difluorocyclohexyl)methyl]-8-fluoroimidazo[1,2-a] pyridin-7-yl}acetate To a solution of Intermediate 10 (90%, 100 mg, 0.18 mmol) in anhydrous THF (1.8 mL) were added allylpalladium(II) chloride (3.3 mg, 9.02 μmol) and XPhos (8.6 mg, 0.018 mmol). The mixture was sonicated and purged with nitrogen for 5 minutes. tert-Butyl 2-(bromozincio)acetate (0.5M in THF, 1.1 mL, 0.55 mmol) was added. The mixture was sonicated and purged with nitrogen for 5 minutes. The reaction mixture was sealed under nitrogen and heated at 50° C. for 3 h, then stood at r.t. overnight. Additional portions of allylpalladium(II) chloride (3.3 mg, 9.02 μmol) and XPhos (8.6 mg, 0.018 mmol) were added, followed by tert-butyl 2-(bromozincio)acetate (0.5M in THF, 2.2 mL, 1.10 mmol), and the mixture was sealed under nitrogen and heated at 50° C. for an additional 18 h. After cooling to r.t., the mixture was quenched with saturated aqueous ammonium chloride solution (20 mL) and partitioned with ethyl acetate (20 mL). The mixture was filtered through a Celite® pad, and washed with ethyl acetate (2×10 mL). The biphasic filtrate was separated, and the aqueous layer was extracted with ethyl acetate (2×30 mL). The combined organic extracts were washed with brine (30 mL), dried over magnesium sulfate and concentrated in vacuo. The resulting crude brown powder (137 mg) was purified by FCC (25 g Biotage Isolera Sfar Dup column), eluting with 10-100/0 EtOAc in heptane, to afford the title compound (56 mg, 48%) as an off-white wax. $\delta_H$ (400 MHz, DMSO-d$_6$) 8.29 (d, J 6.9 Hz, 1H), 7.85 (d, J 3.1 Hz, 1H), 7.49-7.24 (m, 6H), 6.77 (t, J 6.6 Hz, 1H), 5.08 (d, J 12.7 Hz, 1H), 5.03 (d, J 12.7 Hz, 1H), 4.72 (dd, J 19.1, 7.3 Hz, 1H), 3.67 (d, J 1.5 Hz, 2H), 2.14-1.89 (m, 3H), 1.87-1.58 (m, 4H), 1.43 (s, 9H), 1.48-1.36 (m, 1H), 1.34-1.23 (m, 1H). $^{19}$F NMR (376 MHz, DMSO-d$_6$) δ −90.02 (d, J 233 Hz), −99.38 (d, J 233 Hz), −136.52. HPLC-MS (Method 1): MH+ m/z 532, RT 2.04 minutes.

Intermediate 12 tert-Butyl 2-{2-[(S)-benzyloxycarbonylamino(4,4-difluorocyclohexyl)methyl]-8-fluoroimidazo[1,2-a] pyridin-7-yl]-4,4-difluorobutanoate Lithium diisopropylamide solution (2.0M in THF/heptane/ethylbenzene, 0.62 mL, 1.24 mmol) was added dropwise to a stirred solution of Intermediate 11 (93%, 281 mg, 0.49 mmol) in anhydrous THF (10 mL) at −78° C. under nitrogen. The mixture was stirred at −78° C. for 1 h. 2,2-Difluoroethyl trifluoromethanesulfonate (0.1 mL, 0.75 mmol) was added dropwise, and the stirring was continued at −78° C. for 1.5 h under nitrogen. The reaction mixture was quenched by the addition of saturated aqueous ammonium chloride solution (10 mL) at −78° C. The mixture was allowed to warm to r.t., then diluted with water (20 mL) and extracted with ethyl acetate (3×30 mL). The combined organic extracts were washed with brine (30 mL), dried over magnesium sulfate and concentrated in vacuo. The resulting crude brown viscous oil (380 mg) was purified by FCC (25 g, Biotage Isolera Sfar HC Duo column), eluting with 10-60% EtOAc in heptane, to afford the title compound (174 mg, 56%) as a tan viscous oil. $\delta_H$ (400 MHz, 356 K, DMSO-d6) 8.33 (d, J 7.0 Hz, 1H), 7.87 (d, J 3.1 Hz, 1H), 7.55-7.20 (m, 6H), 6.80 (app. t, J 6.6 Hz, 1H), 6.08 (tt, $^1J_{HF}$ 56.2 Hz, J 4.3 Hz, 1H), 5.08 (d, J 12.7 Hz, 1H), 5.03 (d, J 12.7 Hz, 1H), 4.72 (dd, J 8.7, 7.8 Hz, 1H), 4.14 (t, J 7.3 Hz, 1H), 2.76-2.58 (m, 1H), 2.42-2.25 (m, 1H), 2.12-1.91 (m, 3H), 1.88-1.58 (m, 4H), 1.39 (s, 9H), 1.50-1.14 (m, 2H). $^{19}$F NMR (376 MHz, 356 K, DMSO-d$_6$) δ −90.03 (d, J 233.0 Hz), −99.37 (d, J 233.0 Hz), −114.97 (d, J 282.6 Hz), −116.09 (d, J 282.7 Hz), −136.67, −136.69. HPLC-MS (Method 4): MH+ m/z 596, RT 3.49 minutes.

Intermediate 13 tert-Butyl 2-{2-[(S)-amino(4,4-difluorocyclohexyl) methyl]-8-fluoroimidazo[1,2-a]-pyridin-7-yl}-4,4-difluorobutanoate A suspension of Intermediate 12 (93%, 174 mg, 0.27 mmol) and 10% palladium on carbon (50% water wet) (40 mg, 0.019 mmol) in ethanol-water (9:1, 4 mL) was placed under a hydrogen atmosphere and stirred at 20° C. for 20 h. The flask was evacuated and back-filled three times with nitrogen, then the solids were removed by filtration through a Celite® pad, washing with ethanol (4×20 mL). The filtrate was concentrated in vacuo to afford the title compound (1:1 mixture of diastereomers) (132 mg, 98%) as a brown viscous oil, which was utilised without further purification. $\delta_H$ (400 MHz, DMSO-d6) 8.42 (d, J 7.0 Hz, 1H), 7.99 (d, J 2.6 Hz, 1H), 6.88 (t, J 6.6 Hz, 1H), 6.28-5.91 (m, 1H), 4.21-4.11 (m, 2H), 2.75-2.28 (obs. m, 2H), 2.10-1.50 (m, 7H), 1.45-1.13 (m, 2H), 1.36 (s, 9H, Isomer 1), 1.35 (s, 9H, Isomer 2). $^{19}$F NMR (376 MHz, DMSO-d$_6$) −89.91 (d, J 232.5 Hz), −99.74 (d, J 231.8 Hz), −115.07 (d, J 281.5 Hz), −115.16 (d, J 281.7 Hz), −116.31 (d, J 281.6 Hz), −116.34 (d, J 281.6 Hz), −137.00, −137.05. HPLC-MS (Method 1): MH+ m/z 462, RT 2.97 minutes (86% purity).

Intermediate 14 tert-Butyl 2-(2-{(S)-(4,4-difluorocyclohexyl)[(4-ethyl-1,2,5-oxadiazole-3-carbonyl)-amino]methyl}-8-fluoroimidazo[1,2-a]pyridin-7-yl)-4,4-difluorobutanoate DIPEA (125 μL, 0.72 mmol) was added to a stirred solution of 4-ethyl-1,2,5-oxadiazole-3-carboxylic acid (49 mg, 0.34 mmol) and HATU (141 mg, 0.37 mmol) in DCM (1.5 mL) at 20° C. The mixture was stirred at 20° C. for 10 minutes under nitrogen. The resultant orange solution was added to a stirred solution of Intermediate 13 (93%, 132 mg, 0.27 mmol) in DCM (1.5 mL) at 20° C. The mixture was stirred for 20 h under nitrogen, then quenched with saturated aqueous sodium carbonate solution (5 mL) and extracted with DCM (4×5 mL), using a hydrophobic frit to separate the phases. The organic filtrate was concentrated in vacuo. The resulting crude orange viscous oil (234 mg) was separated by FCC (25 g Biotage isolera Sfar Duo column, eluant: 0-60% ethyl acetate in heptane) to afford the title compound (1:1 mixture of diastereomers) (118 mg, 68%) as an orange powder, which was utilised without further purification. $\delta_H$ (400 MHz, DMSO-d$_6$) 9.51 (d, J 8.9 Hz, 1H), 8.40 (d, J 7.1 Hz, 1H), 8.00 (d, J 3.1 Hz, 1H), 6.85 (t, J 6.5 Hz, 1H), 6.09 (tt, $^1J_{HF}$ 56.0, J 4.4 Hz, 1H), 5.14 (t, J 8.6 Hz, 1H), 4.13 (t, J 7.3 Hz, 1H), 2.89 (q, J 7.4 Hz, 2H), 2.72-2.54 (m, 1H), 2.41-2.25 (m, 1H), 2.25-2.14 (m, 1H), 2.10-1.55 (m, 6H), 1.45-1.31 (m, 1H), 1.35 (s, 9H, Isomer 1), 1.35 (s, 9H, Isomer 2), 1.21 (t, J 7.5 Hz, 3H, Isomer 1), 1.21 (t, J 7.5 Hz, 3H, Isomer 2), 1.31-1.13 (m, 1H). $^{19}$F NMR (376 MHz, DMSO-d$_6$) −90.17 (d, J 232.5 Hz), −99.53 (d, J 230.6 Hz), −115.24 (d, J 281.8 Hz, Isomer 1), −115.25 (d, J 281.8 Hz. Isomer 2), −116.29 (d, J 281.8 Hz), −137.08 (Isomer 1), −137.10 (Isomer 2). HPLC-MS (Method 1): MH+ m/z 586, RT 2.08 minutes (96% purity).

Intermediate 15

2-(2-{(S)-(4,4-Difluorocyclohexyl)[(4-ethyl-1,2,5-oxadiazole-3-carbonyl)amino]methyl}-8-fluoroimidazo[1,2-a]pyridin-7-yl)-4,4-difluorobutanoic acid Trifluoroacetic acid (0.54 mL, 7.27 mmol) was added to a stirred solution of Intermediate 14 (90%, 118 mg, 0.18 mmol) in DCM (2 mL). The mixture was stirred at 20° C. for 20 h, then concentrated in vacuo. The residue was azeotroped with DCM (3×10 mL) and chloroform (1×5 mL), then dried under high vacuum at 40° C. for 2 h, to afford the title compound (TFA salt) (1:1 mixture of diastereomers) (118 mg, 91%) as a tan powder, which was utilised without further perification. $\delta_H$ (400 MHz, DMSO-d$_6$) 13.04 (br s, 1H), 9.53 (d, J 8.9 Hz, 1H, Isomer 2), 9.52 (dd, J 8.0, 6.8 Hz, 1H, Isomer 1), 8.43 (d, J 7.0 Hz, 1H), 8.03 (d, J 2.9 Hz, 1H), 6.93 (t, J 6.6 Hz, 1H), 6.09 (tt, $^1J_{HF}$ 56.2, J 4.3 Hz, 1H), 5.15 (t, J 8.6 Hz, 1H), 4.16 (dd, J 7.9, 6.8 Hz, 1H), 2.89 (q, J 7.5 Hz, 2H), 2.75-2.57 (m, 1H), 2.42-2.27 (m, 1H), 2.27-2.13 (m, 1H), 2.12-1.53 (m, 6H), 1.46-1.10 (m, 2H), 1.22 (t, J 7.5 Hz, 3H). $^{19}$F NMR (376 MHz, DMSO-d$_6$) −74.86, −90.21 (d, J 233.0 Hz), −99.55 (d, J 232.9 Hz), −115.03 (d, J 281.7 Hz, Isomer 2), −115.04 (d, J 281.7 Hz, Isomer 1), −116.40 (d, J 281.3 Hz, Isomer 2), −116.42 (d, J 281.7 Hz, Isomer 1), −136.96. HPLC-MS (Method 1): MH+ m/z 530, RT 1.85 minutes (98% purity).

Example 1

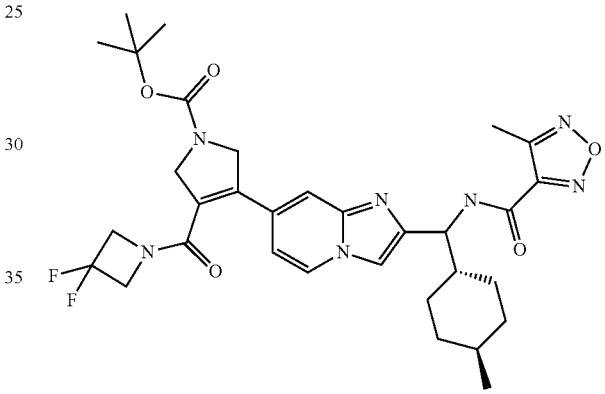

tert-Butyl 3-(3,3-difluoroazetidine-1-carbonyl)-4-(2-{(4-trans-methylcyclohexyl)[(4-methyl-1,2,5-oxadiazole-3-carbonyl)amino]methyl}imidazo[1,2-a]pyridin-7-yl)-2,5-dihydropyrrole-1-carboxylate Intermediate 6 (316 mg. 0.615 mmol) was dissolved in DCM (20 mL), then DIPEA (0.15 mL, 2.15 mmol), HATU (214 mg, 0.738 mmol) and 3,3-difluoroazetidine hydrochloride (72 mg, 0.738 mmol) were added. The mixture was stirred at ambient temperature for 1 h, then diluted with DCM (50 mL) and brine (25 mL). The organic layer was separated using a hydrophobic PTFE frit, then concentrated in vacuo. The crude material was purified by flash column chromatography, eluting with EtOAc in isohexanes (0-100%). The residue was further purified by preparative HPLC (Method 3) to afford the title compound (5 mg, 2%) as a white solid. $\delta_H$ (400 MHz, CDCl$_3$) 8.06 (dd, J 7.0, 2.8 Hz, 1H), 7.64 (t, J 9.1 Hz, 1H), 7.55 (s, 1H), 7.51 (dd, J 4.3, 1.6 Hz, 1H), 6.95-6.74 (m, 1H), 5.21-5.04 (m, 1H), 4.71-4.47 (m, 4H), 4.47-4.28 (m, 2H), 4.21-3.89 (m, 2H), 2.60 (d, J 1.2 Hz, 3H), 2.08-1.86 (m, 2H), 1.70 (dd, J 34.6, 12.9 Hz, 2H), 1.50 (d, J 3.6 Hz, 9H), 1.37-1.24 (m, 2H), 1.23-0.88 (m, 4H), 0.86 (d, J 6.5 Hz, 3H). HPLC-MS (ES+) (Method 2): MH+ m/z 640.4, RT 2.41 minutes.

Example 2

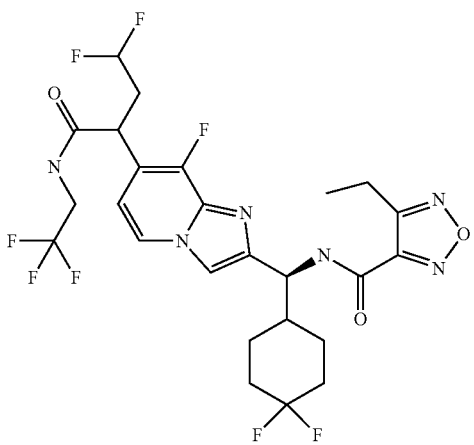 [SMILES: CCc1nonc1C(=O)N[C@H](c1cn2ccc(C(CC(F)F)C(=O)NCC(F)(F)F)c(F)c2n1)C1CCC(F)(F)CC1]

N—[(S)-(4,4-Difluorocyclohexyl)-{7-[3,3-difluoro-1-(2,2,2-trifluoroethylcarbamoyl)-propyl]-8-fluoro-imidazo[1,2-a]pyridin-2-yl}methyl]-4-ethyl-1,2,5-oxadiazole-3-carboxamide A solution of Intermediate 15 (117 mg, 0.18 mmol) in DMA (1.2 mL) was added dropwise to a stirred solution of 2,2,2-trifluoroethylamine (25.7 μL, 0.33 mmol), 2-chloro-1-methylpyridinium iodide (60.3 mg, 0.24 mmol) and DIPEA (158 μL, 0.91 mmol) in DMA (1.2 mL). The mixture was heated at 40° C. in a sealed vial for 40 minutes. After cooling, the mixture was partitioned between brine (5 mL), water (20 mL) and ethyl acetate (30 mL). The organic phase was separated, and the aqueous layer was extracted with ethyl acetate (2×30 mL). The combined organic extracts were washed with brine (2×20 mL), dried over magnesium sulfate and concentrated in vacuo. The resulting crude brown viscous oil (118 mg) was separated by low pH preparative HPLC (formic acid-water-acetonitrile) to afford, after freeze drying, the title compound (1:1 mixture of diastereomers) (57 mg, 51%) as an off-white powder. $\delta_H$ (400 MHz, DMSO-$d_6$) 9.50 (d, J 8.9 Hz, 1H), 8.94-8.80 (m, 1H), 8.37 (d, J 7.1 Hz, 1H), 8.03-7.92 (m, 1H), 6.84 (t, J 6.5 Hz, 1H), 6.04 (tt, $^1J_{HF}$ 55.9, J 4.1 Hz, 1H), 5.14 (t, J 8.6 Hz, 1H), 4.21 (t, J 7.2 Hz, 1H), 4.00-3.77 (m, 2H), 2.89 (q, J 7.5 Hz, 2H), 2.71-2.54 (m, 1H), 2.37-2.11 (m, 2H), 2.11-1.66 (m, 5H), 1.65-1.52 (m, 1H), 1.46-1.15 (m, 2H), 1.22 (t, J 7.5 Hz, 3H). $^{19}F$ NMR (376 MHz, DMSO-$d_6$) −70.66, −90.19 (d, J 232.7 Hz), −99.52 (d, J 232.4 Hz), −115.09 (d, J 281.8 Hz), −116.37 (d, J 281.7 Hz, Isomer 1), −116.38 (d, J 281.8 Hz, Isomer 2), −136.17. HPLC-MS (Method 5): MH+ m/z 611, RT 3.64 minutes (100% purity).

The invention claimed is:

1. A compound represented by formula (I-1) or an N-oxide thereof, or a pharmaceutically acceptable salt thereof:

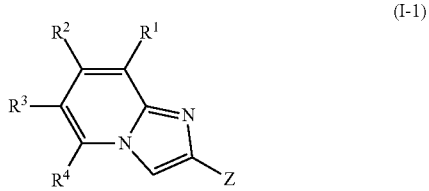

(I-1)

wherein
Z represents —CH ($R^5$)N(H)C(O)$R^6$;
$R^1$ represents hydrogen or halogen;
$R^2$ represents $C_{1-6}$ alkyl or $C_{3-7}$ heterocycloalkenyl, either of which groups is optionally substituted by one or more substituents;
$R^3$ represents hydrogen;
$R^4$ represents hydrogen;
$R^5$ represents $C_{3-9}$ cycloalkyl, which group is optionally substituted by one, two or three substituents independently selected from hydrogen, halogen and $C_{1-6}$ alkyl; and
$R^6$ represents heteroaryl, which group is optionally substituted by one, two or three substituents independently selected from $C_{1-6}$ alkyl.

2. A compound as claimed in claim 1 represented by formula (IIA) or an N-oxide thereof, or a pharmaceutically acceptable salt thereof:

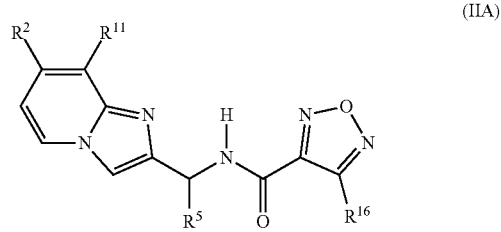

(IIA)

wherein
$R^{11}$ represents hydrogen or halogen; and
$R^{16}$ represents methyl or ethyl.

3. A compound as claimed in claim 2 wherein $R^{11}$ represents fluoro.

4. A compound as claimed in claim 1 which is
tert-Butyl 3-(3,3-difluoroazetidine-1-carbonyl)-4-(2- {(4-trans-methylcyclohexyl)[(4-methyl-1,2,5-oxadiazole-3-carbonyl)amino]methyl}imidazo[1,2-a]pyridin-7-yl)-2,5-dihydropyrrole-1-carboxylate; or
N-[(S)-(4,4-Difluorocyclohexyl){7-[3,3-difluoro-1-(2,2,2-trifluoroethylcarbamoyl)-propyl]-8-fluoroimidazo[1,2-a] pyridin-2-yl}methyl]-4-ethyl-1,2,5-oxadiazole-3-carboxamide;
or a pharmaceutically acceptable salt thereof.

5. A pharmaceutical composition comprising a first pharmaceutically active ingredient which is a compound of formula (I-1) as defined in claim 1 or an N-oxide thereof, or a pharmaceutically acceptable salt thereof, and a pharmaceutically acceptable carrier.

6. A pharmaceutical composition as claimed in claim 5 further comprising an additional pharmaceutically active ingredient.

7. A method for the treatment of disorders for which the administration of a modulator of IL-17 function is indicated which comprises administering to a patient in need of such treatment an effective amount of a compound of formula (I-1) as defined in claim 1 or an N-oxide thereof, or a pharmaceutically acceptable salt thereof.

8. A method for the treatment of psoriasis, psoriatic arthritis or ankylosing spondylitis, which comprises administering to a patient in need of such treatment an effective amount of a compound of formula (I-1) as defined in claim 1 or an N-oxide thereof, or a pharmaceutically acceptable salt thereof.

9. A compound as claimed in claim 1 wherein the group represented by $R^2$ is optionally substituted by one, two or three substituents independently selected from halogen, $C_{2-6}$ alkoxycarbonyl, trifluoroethyl-aminocarbonyl and difluoroazetidinylcarbonyl.

10. A compound as claimed in claim 1 wherein $R^2$ represents (difluoro) (trifluoroethylaminocarbonyl) propyl or (tert-butoxycarbonyl)(difluoroazetidinylcarbonyl)-2,5-dihydropyrrolyl.

\* \* \* \* \*